(12) United States Patent
Yamaji

(10) Patent No.: US 10,667,758 B2
(45) Date of Patent: Jun. 2, 2020

(54) SENSOR INFORMATION PROCESSING APPARATUS

(71) Applicant: FUJITSU LIMITED, Kawasaki-shi, Kanagawa (JP)

(72) Inventor: Takayuki Yamaji, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 228 days.

(21) Appl. No.: 15/415,363

(22) Filed: Jan. 25, 2017

(65) Prior Publication Data

US 2017/0215813 A1   Aug. 3, 2017

(30) Foreign Application Priority Data

Feb. 2, 2016  (JP) ................. 2016-018222

(51) Int. Cl.
| | |
|---|---|
| *A61B 5/00* | (2006.01) |
| *A61B 5/024* | (2006.01) |
| *A61B 5/11* | (2006.01) |
| *A61B 5/0205* | (2006.01) |
| *A61B 5/0402* | (2006.01) |
| *A61B 5/0245* | (2006.01) |

(52) U.S. Cl.
CPC ............ *A61B 5/7278* (2013.01); *A61B 5/002* (2013.01); *A61B 5/0022* (2013.01); *A61B 5/024* (2013.01); *A61B 5/0205* (2013.01); *A61B 5/0402* (2013.01); *A61B 5/11* (2013.01); *A61B 5/112* (2013.01); *A61B 5/1118* (2013.01); *A61B 5/721* (2013.01); *A61B 5/0245* (2013.01); *A61B 5/02433* (2013.01)

(58) Field of Classification Search
CPC ....... A61B 5/024; A61B 5/1118; A61B 5/112; A61B 5/0205; A61B 5/11
See application file for complete search history.

(56) References Cited

U.S. PATENT DOCUMENTS

| | | | | |
|---|---|---|---|---|
| 5,924,980 | A | * | 7/1999 | Coetzee ............ A61B 5/14551 128/901 |
| 9,874,933 | B1 | * | 1/2018 | Carryer ................... G06F 3/013 |
| 2004/0039420 | A1 | * | 2/2004 | Jayne .................... A61B 5/1107 607/5 |
| 2004/0077954 | A1 | * | 4/2004 | Oakley ................ A61B 5/0006 600/483 |
| 2005/0065443 | A1 | * | 3/2005 | Ternes ................. A61B 5/0006 600/509 |
| 2005/0113703 | A1 | * | 5/2005 | Farringdon .......... A61B 5/0428 600/509 |

(Continued)

FOREIGN PATENT DOCUMENTS

| | | |
|---|---|---|
| CN | 102764111 A | 11/2012 |
| CN | 104602595 A | 5/2015 |

(Continued)

OTHER PUBLICATIONS

Extended European Search Report dated Jun. 30, 2017 for corresponding European Patent Application No. 17153265.8, 6 pages.

(Continued)

*Primary Examiner* — Sean P Dougherty
(74) *Attorney, Agent, or Firm* — Fujitsu Patent Center

(57) ABSTRACT

A target frequency band to be processed in a detected signal of a heartbeat sensor is controlled according to a detected signal of an inertial sensor.

9 Claims, 22 Drawing Sheets

(56) References Cited

U.S. PATENT DOCUMENTS

| | | | |
|---|---|---|---|
| 2009/0082681 A1 | 3/2009 | Yokoyama et al. | |
| 2011/0251495 A1* | 10/2011 | Province | A61B 5/01 600/483 |
| 2012/0123232 A1* | 5/2012 | Najarian | A61B 5/0022 600/345 |
| 2012/0215115 A1* | 8/2012 | Takahashi | A61B 5/02416 600/483 |
| 2012/0277605 A1* | 11/2012 | Colborn | A61B 5/024 600/508 |
| 2012/0283525 A1 | 11/2012 | Kuroda | |
| 2013/0006123 A1 | 1/2013 | Aoshima | |
| 2014/0024917 A1* | 1/2014 | McMahon | A61B 5/4836 600/407 |
| 2014/0275852 A1 | 9/2014 | Hong et al. | |
| 2014/0275854 A1* | 9/2014 | Venkatraman | A61B 5/721 600/301 |
| 2015/0018636 A1* | 1/2015 | Romesburg | A61B 5/721 600/301 |
| 2015/0173627 A1 | 6/2015 | Fujii et al. | |
| 2015/0351646 A1* | 12/2015 | Cervini | A61B 5/6824 600/479 |
| 2015/0374240 A1* | 12/2015 | Lee | A61B 5/0205 600/483 |
| 2016/0007935 A1* | 1/2016 | Hernandez | A61B 5/7278 600/301 |
| 2016/0029968 A1* | 2/2016 | Lerner | A61B 5/7217 600/301 |
| 2016/0030806 A1* | 2/2016 | Matsumoto | A61B 5/4519 600/301 |
| 2016/0120476 A1* | 5/2016 | Liu | A61B 5/721 600/479 |
| 2016/0249820 A1* | 9/2016 | Puig | A61B 5/02416 600/479 |
| 2016/0324477 A1* | 11/2016 | Gunturi | A61B 5/721 |
| 2016/0367201 A1* | 12/2016 | Korsower | A61B 5/0205 |
| 2017/0164847 A1* | 6/2017 | Pande | A61B 5/0002 |
| 2017/0238875 A1* | 8/2017 | Olivier | A61B 5/7207 |
| 2017/0245784 A1* | 8/2017 | Yamaji | A61B 7/04 |
| 2018/0014778 A1* | 1/2018 | Cronin | G06F 19/3418 |
| 2018/0085069 A1* | 3/2018 | Murali | A61B 5/0205 |

FOREIGN PATENT DOCUMENTS

| | | |
|---|---|---|
| EP | 2229880 A1 | 9/2010 |
| EP | 2520222 A1 | 11/2012 |
| JP | 01-115344 | 5/1989 |
| JP | 2008-125595 | 6/2008 |
| JP | 2009-072417 | 4/2009 |
| JP | 2011-115459 | 6/2011 |
| JP | 2012-130391 | 7/2012 |
| JP | 2014-54447 A | 3/2014 |
| JP | 2014-54448 A | 3/2014 |
| JP | 2014-094043 | 5/2014 |
| WO | 2015/139930 A1 | 9/2015 |
| WO | 2015129557 A1 | 9/2015 |
| WO | 2015/199865 A1 | 12/2015 |

OTHER PUBLICATIONS

European Office Action dated Jun. 4, 2019 for corresponding European Patent Application No. 17153265.8, 5 pages.
Chinese Office Action dated Jun. 26, 2019 for corresponding Chinese Patent Application No. 201710061817.3, with English Translation, 20 pages.
Japanese Office Action dated Aug. 20, 2019 for corresponding Japanese Patent Application No. 2016-018222, with English Translation, 8 pages.
Chinese Office Action dated Mar. 10, 2020 for corresponding Chinese Patent Application No. 201710061817.3, with English Translation, 22 pages.

* cited by examiner

FIG. 11

| METs | km/h |
|---|---|
| 1.0 | 0.0 |
| 1.5 | 1.5 |
| 3.0 | 2.5 |
| 3.3 | 3.0 |
| 3.8 | 3.5 |
| 5.0 | 4.0 |
| 6.3 | 4.5 |
| 7.0 | 5.0 |
| 8.0 | 6.6 |
| 9.0 | 8.4 |
| 10.0 | 9.7 |
| 11.0 | 10.8 |
| 15.0 | 14.5 |

FIG. 18

| | HEART RATE NEAR 60 | HEART RATE NEAR 120 |
|---|---|---|
| THE NUMBER OF SAMPLES | 532 | 532 |
| AVERAGE VALUE Xbar | -0.000652964 | 0.000556391 |
| SAMPLE STANDARD DEVIATION σ | 0.041438026 | 0.025446051 |
| MINIMUM VALUE Min | -0.10593357 | -0.103 |
| MAXIMUM VALUE Max | 0.134123404 | 0.096 |
| RANGE R | 0.240056974 | 0.199 |
| SKEW | 0.383 | -0.571 |
| KURTOSIS | -0.097 | 2.991 |
| BPF LOWER LIMIT | -0.165 | -0.165 |
| BPF UPPER LIMIT | 0.165 | 0.165 |
| CP | 1.33 | 2.16 |
| CPK | 1.32 | 2.15 |

FIG. 19

| | HEART RATE NEAR 60 | HEART RATE NEAR 120 |
|---|---|---|
| THE NUMBER OF SAMPLES | 532 | 532 |
| AVERAGE VALUE Xbar | −0.000652964 | 0.000556391 |
| SAMPLE STANDARD DEVIATION σ | 0.041438026 | 0.025446051 |
| MINIMUM VALUE Min | −0.10593357 | −0.103 |
| MAXIMUM VALUE Max | 0.134123404 | 0.096 |
| RANGE R | 0.240056974 | 0.199 |
| SKEW | 0.383 | −0.571 |
| KURTOSIS | −0.097 | 2.991 |
| BPF LOWER LIMIT | −0.1015 | −0.1015 |
| BPF UPPER LIMIT | 0.1015 | 0.1015 |
| CP | 0.82 | 1.33 |
| CPK | 0.81 | 1.32 |

FIG. 22

BANDWIDTH INFORMATION 170

| REFERENCE HEART RATE [bpm] | BPF WIDTH LOWER LIMIT [Hz] | BPF WIDTH UPPER LIMIT [Hz] |
|---|---|---|
| 40 | 0.366666667 | 0.966666667 |
| 50 | 0.543333333 | 1.123333333 |
| 60 | 0.72 | 1.28 |
| 70 | 0.896666667 | 1.436666667 |
| 80 | 1.073333333 | 1.593333333 |
| 90 | 1.25 | 1.75 |
| 100 | 1.426666667 | 1.906666667 |
| 110 | 1.603333333 | 2.063333333 |
| 120 | 1.78 | 2.22 |

SENSOR INFORMATION PROCESSING APPARATUS

CROSS-REFERENCE TO RELATED APPLICATION

This application is based upon and claims the benefit of priority of the prior Japanese Patent Application No. 2016-018222, filed on Feb. 2, 2016, the entire contents of which are incorporated herein by reference.

FIELD

The embodiment(s) discussed herein is related to a sensor information processing apparatus.

BACKGROUND

There is a technique of detecting a heartbeat of a biological object by using a heartbeat sensor. A bandpass filter (BPF) is applied to a detected signal of the heartbeat sensor to detect a signal component corresponding to the heartbeat from the detected signal of the heartbeat sensor.

Further, a heartbeat of a biological object varies in a time length of one heartbeat according to whether a heart rate per unit time is high or low. Therefore, BPF characteristics (e.g. pass center frequency and a passband width) may be varied depending on whether the heart rate is high or low.

RELATED ART DOCUMENTS LIST

Patent Document 1 JP2009-72417 A
Patent Document 2 JP2012-130391 A
Patent Document 3 JP1-115344 A
Patent Document 4 JP2011-115459 A
Patent Document 5 JP2008-125595 A
Patent Document 6 JP2014-94043 A When a motion of a biological object occurs, a signal component derived from the body motion (hereinafter, may be referred to as a "body motion derived signal component) would be included in a detected signal of a heartbeat sensor in addition to a signal component derived from a heartbeat (hereinafter, may be referred to as a "heartbeat signal"). The body motion derived signal component may be a noise component for the heartbeat signal to be detected.

Hence, even when BPF characteristics are varied according to whether a heart rate detected from a detected signal of a heartbeat sensor is high or low, the BPF characteristics do not become appropriate for detection of a heartbeat derived signal component. Hence, a detection accuracy of heartbeat signal would lowers.

SUMMARY

In one aspect, a sensor information processing apparatus may include a receiver and a processor. The receiver may receive a detected signal of a heartbeat sensor and a detected signal of an inertial sensor. The processor may control a target frequency band to be processed in the detected signal of the heartbeat sensor according to the detected signal of the inertial sensor.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 11 is a diagram illustrating an example of a relationship between a walking speed and an exercise intensity (METs value) according to one embodiment;

FIGS. 18 and 19 are diagrams illustrating examples of a statistical process of the heart rate according to an embodiment;

FIG. 22 is a diagram illustrating an example of bandwidth information of the BPF according to an embodiment.

DESCRIPTION OF EMBODIMENTS

Figure 1:
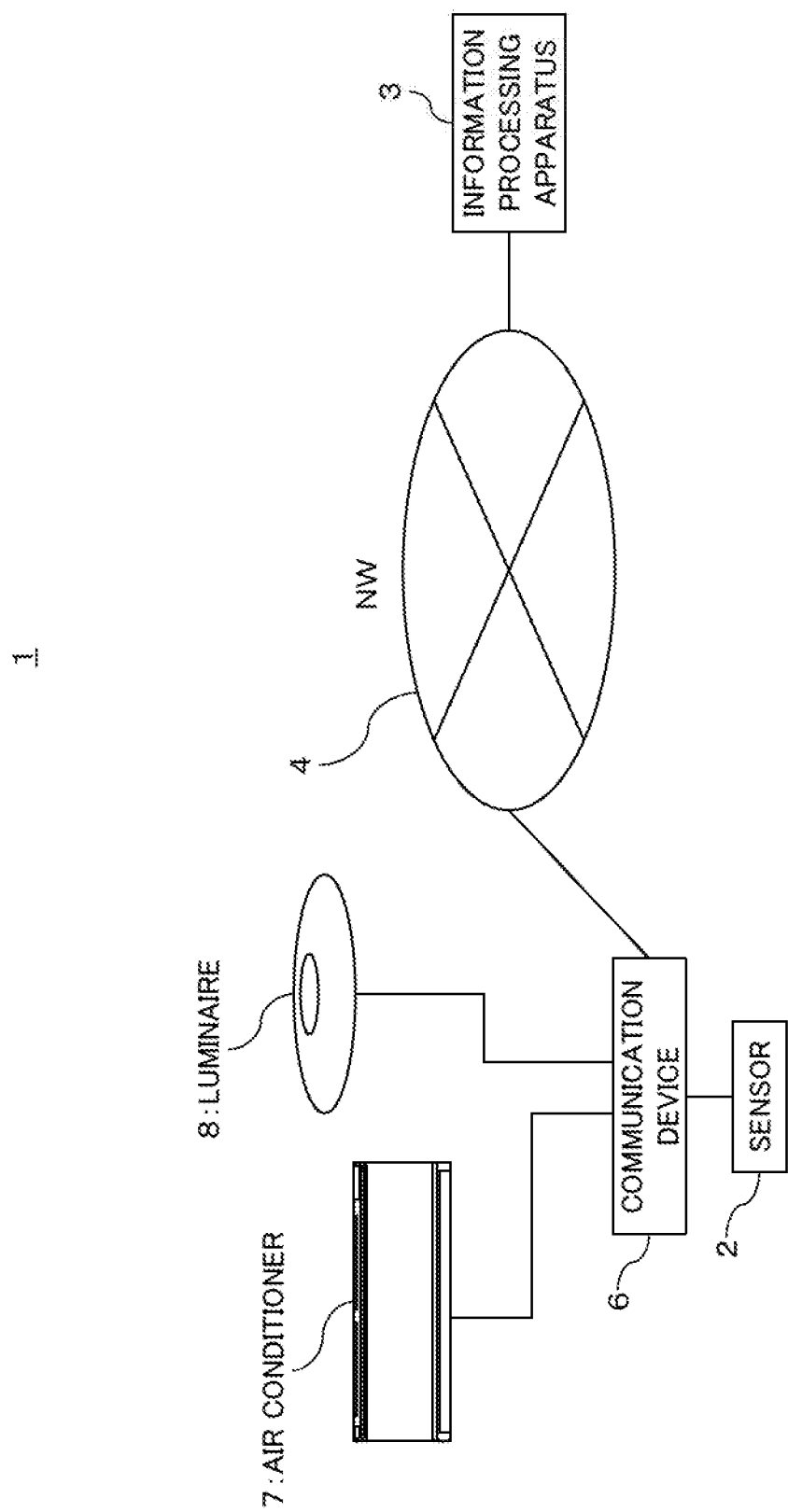
FIG. 1 is a block diagram illustrating an example of a sensor system according to an embodiment.

Hereinafter, an exemplary embodiment (s) will be described with reference to the drawings. However, the embodiment(s) described below is merely an example and not intended to exclude an application of various modifications or techniques which are not explicitly described below. Further, various exemplary aspects described below may be appropriately combined and carried out. Elements or components assigned the same reference numeral in the drawings used for the following embodiment(s) will represent identical or similar elements or components unless otherwise specified.

FIG. 1 is a block diagram illustrating an example of a sensor system according to an embodiment. A sensor system 1 illustrated in FIG. 1 may illustratively include a vital sensor 2, an information processing apparatus 3 and a network (NW) 4.

The vital sensor 2 may illustratively be connected to the network 4 through a communication device 6, and may be available to communicate with the information processing apparatus 3 through the network 4.

The vital sensor 2 is available to sense information of a biological object (hereinafter, may be referred to as "vital information"). The biological object is an example of a sensing target. The term of "sensing" may be referred to as "detection" or "measurement".

A non-restrictive example of the "vital information" is information indicative of a heartbeat of a biological object. Since a blood vessel of the biological object pulsates according to a heartbeat, the information indicative of the heartbeat may be considered as being equivalent to information indicative of a pulsebeat.

The heartbeat or the pulsebeat of the biological object can be illustratively acquired as a change in an electromagnetic wave, a pressure or sound corresponding to a heartbeat.

For example, when a blood vessel of a finger or an earlobe is irradiated with light such as infrared rays, the reflected light would be change periodically according to a rhythmical change in a bloodstream and light absorption characteristics. Hence, a heartbeat or a pulsebeat can be optically measured as a fluctuation of reflected light according to a change in a bloodstream.

Alternatively, when a biological object is irradiated with a radio wave such as a microwave, a rhythmical motion would occur in a surface of a biological object (e.g. skin) according to a heartbeat. Therefore, a distance between the skin and a radio wave transmission source changes according to the motion, and changes due to a Doppler effect would occur in a reflected wave. Hence, it is also possible to measure a heartbeat or a pulsebeat as a fluctuation caused by the Doppler effect of the reflected wave irradiated on the biological object.

Further, when a heart is contracted and relaxed rhythmically, a pressure of a blood vessel (hereinafter, may be referred to as a "blood pressure") would also be fluctuated. Therefore, it is also possible to measure a heartbeat or a pulsebeat as a rhythmical fluctuation of a blood pressure by using a pressure sensor or a piezoelectric sensor.

Furthermore, it is also possible to measure a heartbeat as a change in an electric potential or a change in sound of a heart muscle corresponding to a heart pulse by using an electrocardiograph or a phonocardiograph.

A sensor available to measure a heartbeat using any one of the above measurement schemes may be referred to as a "heartbeat sensor" or a "heartbeat meter". As described above, since the information indicative of a "heartbeat" may be considered as being equivalent to the information indicative of a "pulsebeat" in some cases, the "heartbeat sensor" or the "heartbeat meter" may be referred to as a "pulsebeat sensor" or a "pulsebeat meter".

In the present embodiment, an example where a "wireless sensor" available to measure a heartbeat by using the Doppler effect is applied to the vital sensor 2 as an example of the heartbeat sensor will be described for descriptive purposes. The "wireless sensor" may be referred to as a "microwave sensor", an "RF (Radio Frequency) sensor" or a "Doppler sensor".

The vital sensor 2 may be illustratively attached in contact with a skin of a human body or may be attached to clothes of the human body. The vital sensor 2 does not need to be attached to a human body by way of strictly fixing (may be referred to as "restraining"). A relative motion (which may be referred to as an "asynchronous motion") may be permitted to be made between the vital sensor 2 and a human body according to a mismatch between motions of the clothes and a human body surface.

For example, the vital sensor 2 may be attached to a human body such that the vital sensor 2 is allowed to be moved in one of three-dimensional directions relative to a human body. Illustratively, the vital sensor 2 may be put in a pocket of clothes such as a breast pocket of a jacket or may be attached on the clothes by using an attachment tool such as a harness.

Next, the communication device 6 illustrated in FIG. 1 is available to transmit a sensing result (e.g. the information indicative of the heartbeat) of the vital sensor 2 to the information processing apparatus 3 through the network 4, for example. Hence, the communication device 6 may be connected with the network 4 using a wired cable or radio.

In other words, the communication device 6 may be provided with a communication interface (IF) which supports one or both of wireless and wired communications. Illustratively, a communication scheme based on the LTE (Long Term Evolution) or the LTE-Advanced of 3GPP (3rd Generation Partnership Project) is applicable to the wireless communication of the communication device 6.

Further, satellite communications may be applied to the wireless communication of the communication device 6. When the satellite communication is applied, the communication device 6 may be able to communicate with the information processing apparatus 3 through a communication satellite without being routed through the network 4.

The sensing result of the vital sensor 2 may include not only vital information but also information indicative of a result of an arithmetic operation or determination, which is obtained based on the vital information. The sensing result may be referred to as "sensor information" or "sensor data" for descriptive purposes.

The communication device 6 may be externally attached to the vital sensor 2 as illustrated in FIG. 1, or may be built in the vital sensor 2. The communication device 6 externally attached to the vital sensor 2 may be, for example, a device carried by a person attached with the vital sensor 2. The person attached with the vital sensor 2 may be referred to as a "user", a "subject" or an "observed person" for descriptive purposes.

The communication device 6 carried by the user may be illustratively a mobile telephone (which may include a smartphone), a notebook PC or a tablet PC. The "PC" is an abbreviation of a "personal computer".

A wired connection or a wireless connection may be applied to a connection between the vital sensor 2 and the communication device 6. In other words, the vital sensor 2 may be provided with a communication IF which supports one or both of wireless and wired communications. The "WiFi (Wireless Fidelity)"® or "Bluetooth"® may also be applied to the wireless connection.

The communication device 6 externally attached to the vital sensor 2 may be a router or a network switch. As illustrated in FIG. 1, the communication device 6 may be communicably connected with an air conditioner 7 and an luminaire 8 so that the air conditioner 7 and the luminaire 8 are able to communicate with the information processing apparatus 3 through the network 4.

The network 4 may be illustratively a WAN (Wide Area Network), a LAN (Local Area Network) or the Internet. Further, the network 4 may include a wireless access network. The wireless access network may be compliant with the above-described LTE or LTE-Advanced.

The information processing apparatus 3 receives the sensor information of the vital sensor 2 through the network 4 (or may be through the communication satellite), and processes the received sensor information. Hence, the information processing apparatus 3 may be referred to as the sensor information processing apparatus 3.

Processing the sensor information may include storing and managing the sensor information, and estimating a heart rate of the user based on the sensor information. Hence, the information processing apparatus 3 is available to monitor an activity status of the user, for example. In other words, the sensor system 1 can provide a user "monitoring (or watching) function".

Managing the sensor information may include compiling the sensor information in a database (DB). The data compiled in the DB may be referred to as "cloud data" or "big data".

The information processing apparatus 3 may be illustratively realized by one or a plurality of servers. In other words, the sensor information obtained by the vital sensor 2 may be processed or managed by a single server or may be distributedly processed or managed by a plurality of servers in the information processing apparatus 3. The server may correspond to a cloud server provided in a cloud data sensor, for example.

The information processing apparatus 3 may be communicably connected with the vital sensor 2 without being routed through the network 4. For example, the information processing apparatus 3 may be available to directly receive the sensor information from the vital sensor 2 through a wired cable or by radio.

(Configuration Example of Vital Sensor 2)

Figure 2:
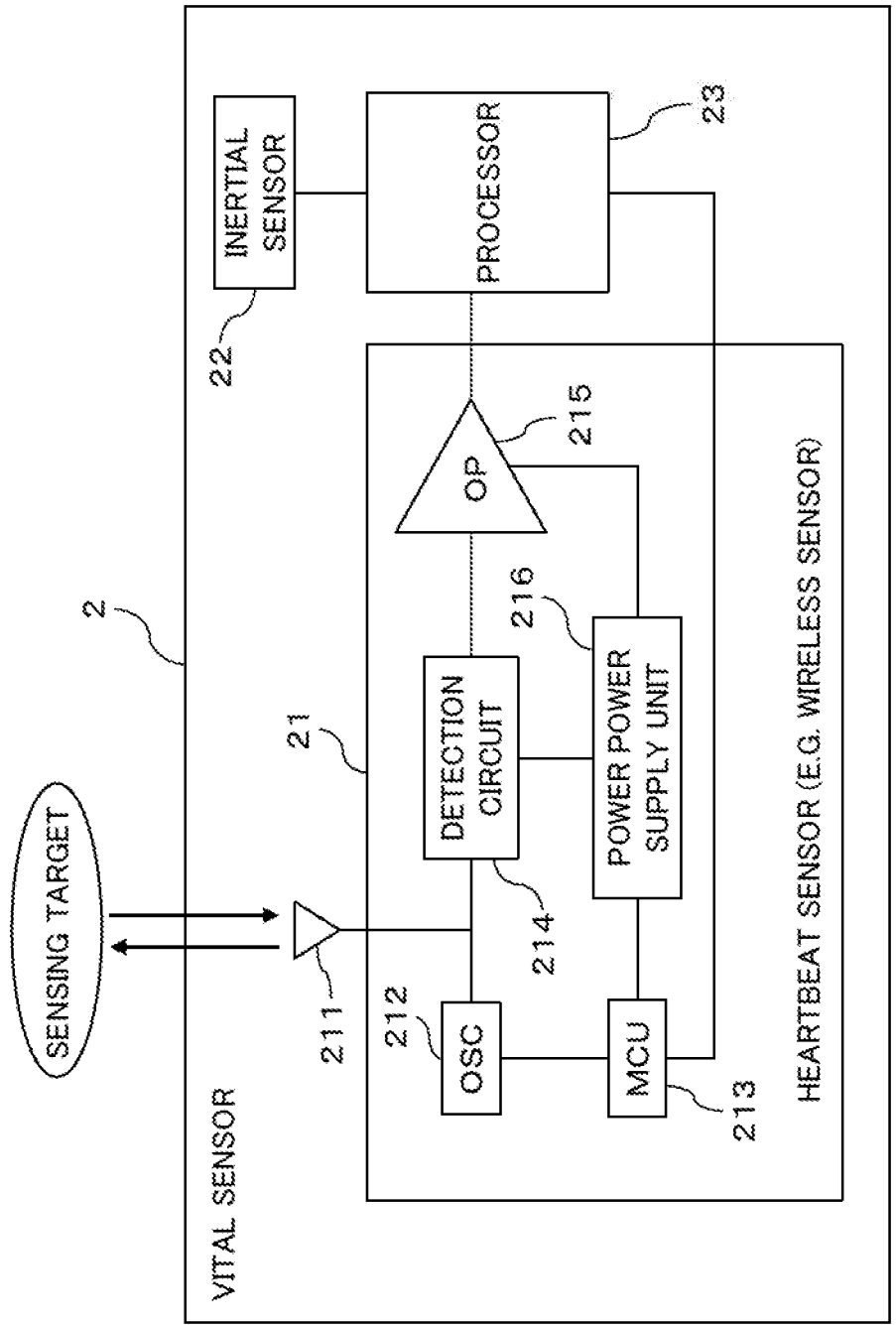
FIGS. 2 and 3 are block diagrams illustrating configuration examples of a vital sensor according to an embodiment.
Figure 3:
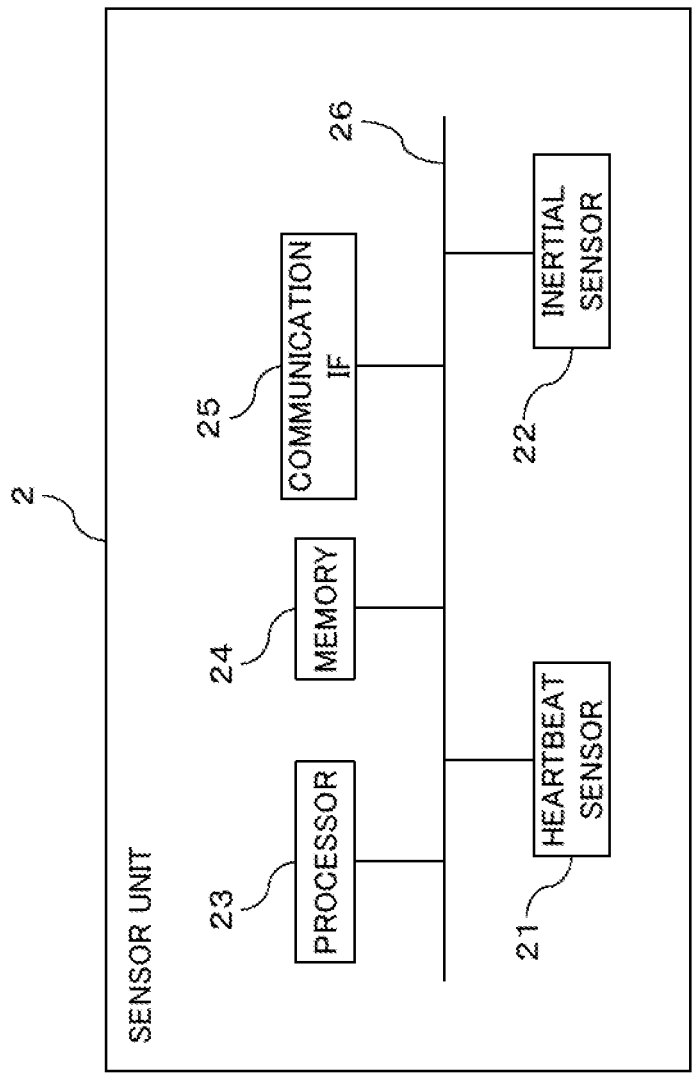

Next, the configuration example of the vital sensor 2 will be described with reference to FIGS. 2 and 3. As illustrated in FIGS. 2 and 3, the vital sensor 2 may illustratively include a wireless sensor 21, an inertial sensor 22, a processor 23, a memory 24 and a communication IF 25.

The vital sensor 2 may be referred to as the sensor unit 2. Hereinafter, the vital sensor 2 or the sensor unit 2 will be simply referred to as the "sensor 2" for descriptive purposes.

As illustrated in FIG. 3, the wireless sensor 21, the inertial sensor 22, the processor 23, the memory 24 and the communication IF 25 may be illustratively connected to a bus 26 to communicate with each other through the processor 23.

The wireless sensor 21 is an example of the heartbeat sensor as described above and may be illustratively a Doppler sensor. The wireless sensor 21 may perform phase detection on a radio wave transmitted to a space and a reflected wave of the transmitted radio wave, and generate a beat signal. The beat signal may be supplied as an output signal of the wireless sensor 21 to the processor 23.

As illustrated in FIG. 2, the wireless sensor 21 may include, for example, an antenna 211, a local oscillator (OSC) 212, a MCU (Micro Control Unit) 213, a detection circuit 214, an operational amplifier (OP) 215 and a power supply unit (or a power supply circuit) 216.

The antenna 211 transmits to the space a radio wave having an oscillation frequency generated by the OSC 212, and receives a reflected wave of the transmitted radio wave reflected by the user positioned in the space. In an example of FIG. 2, the antenna 211 is shared by a transmission and a reception but a transmission antenna and a reception antenna may be provided individually.

The OSC 212 illustratively oscillates in response to a control of the MCU 213 to output a signal with a predetermined frequency (which may be referred to as a "local signal" for descriptive purposes). The local signal is transmitted as a transmission radio wave from the antenna 211, and is inputted to the detection circuit 214.

The oscillation frequency of the OSC 212 (in other words, a frequency of a radio wave transmitted by the wireless sensor 21) may be illustratively a frequency in a microwave band. The microwave band may be illustratively a 2.4 GHz band or a 24 GHz band.

These frequency bands are examples whose indoor use is authorized by the Radio Act in Japan. Frequency bands which are not regulated by the Radio Act may be used for a transmission radio wave of the wireless sensor 21.

The MCU 213 illustratively controls an oscillating operation of the OSC 212 in response to a control of the processor 23.

The detection circuit 214 illustratively performs the phase detection on the reflected wave received by the antenna 211 and the local signal (in other words, the transmission radio wave) from the OSC 212 to output the beat signal. The detection circuit 214 may be replaced with a mixer which mixes a transmission radio wave and a reflected wave. The mixing performed by the mixer may be considered as being equivalent to the phase detection.

In this regard, a change in an amplitude and a change in a frequency occur in the beat signal obtained by the detection circuit 214 due to the Doppler effect according to a heartbeat of the user. In other words, the beat signal includes information indicative of the heartbeat of the user.

The operational amplifier 215 illustratively amplifies the beat signal outputted from the detection circuit 214. The amplified beat signal is inputted to the processor 23.

The power supply unit 216 illustratively supplies drive power to the MCU 213, the detection circuit 214 and the operational amplifier 215.

Meanwhile, the inertial sensor 22 may illustratively detect a motion of the sensor unit 2. The inertial sensor 22 may be an acceleration sensor or a gyroscope. Any one of piezoelectric type and capacitive type sensors may be illustratively applied to the acceleration sensor. Any one of a spin rotor (flywheel) type, an optical type and a vibrating structure type sensors may be applied to the gyroscope.

The inertial sensor 22 may include one or more of detection axes. A gravity component in a direction along one of the detection axes may be detected as an "acceleration" component, for example. A detected signal of the inertial sensor 22 may be inputted to the processor 23.

The processor 23 is an example of an arithmetic processing apparatus with a capability of arithmetic processing. The arithmetic processing apparatus may be referred to as an arithmetic processing device or an arithmetic processing circuit. An integrated circuit (IC) such as an MPU (Micro Processing Unit) or a DSP (Digital Signal Processor) may be illustratively applied to the processor 23 which is an example of the arithmetic processing apparatus. The "processor" may be referred to as a "processing unit", a "controller" or a "computer".

The processor 23 is available to detect the heartbeat of the user based on the detected signal of the wireless sensor 21. A filter may be illustratively applied to the detected signal of the wireless sensor 21 to detect a heartbeat derived signal component (which may be referred to as a "heartbeat component" or a "heartbeat signal") from the detected signal of the wireless sensor 21. The filter of anon-restrictive example may be a bandpass filter (BPF). The processor 23 may determine a state related to a sleep of the user based on the detected heartbeat.

The detected signal of the inertial sensor 22 may be used to control filter characteristics (illustratively, a pass center frequency and passband width) of the above BPF. Controlling the filter characteristics may be considered as controlling a target frequency band to be processed in the detected signal of the wireless sensor 21. An example of a control of the filter characteristics will be described below.

The "pass center frequency" and the "passband width" of the BPF may be referred to simply as a "center frequency" and a "bandwidth", respectively.

The detected signal of the wireless sensor 21 and the detected signal of the inertial sensor 22 may be both referred to as a "detected value" or an "output value". For descriptive purposes, the detected value of the wireless sensor 21 may be referred to as a "wireless sensor value" and the detected value of the inertial sensor 22 may be referred to as an "inertial sensor value".

Further, the above-described detection of the heartbeat and control of the filter characteristics may be performed by a processor 31 of the information processing apparatus 3 (described below with reference to FIG. 4) instead of the processor 23 of the sensor unit 2.

Next, in FIG. 3, the memory 24 is an example of a storage unit or a storage medium provided in the sensor unit 2, and may be a RAM (Random Access Memory) or a flash memory.

A program and data read and used by the processor 23 to operate may be stored in the memory 24. The "program" may be referred to as a "software" or an "application". The "data" may include data generated according to operations of the processor 23.

The communication IF 25 is an example of a communication unit of the sensor unit 2, and is illustratively connected with the communication device 6 (see FIG. 1) and enables communication with the information processing apparatus 3 through the network 4.

For example, the communication IF 25 may transmit the detected signals of the wireless sensor 21 and the inertial sensor 22, and transmit information obtained based on one or both of the detected signals to the information processing apparatus 3.

In other words, the sensor information transmitted from the vital sensor 2 to the information processing apparatus 3 may include measured values of the wireless sensor 21 and the inertial sensor 22, or may include information obtained based on one or both of the measured values.

The communication IF 25 may be connected with the information processing apparatus 3 to directly communicate with the information processing apparatus 3 without being routed through the communication device 6 and/or the network 4.

(Configuration Example of Information Processing Apparatus 3)

Figure 4:
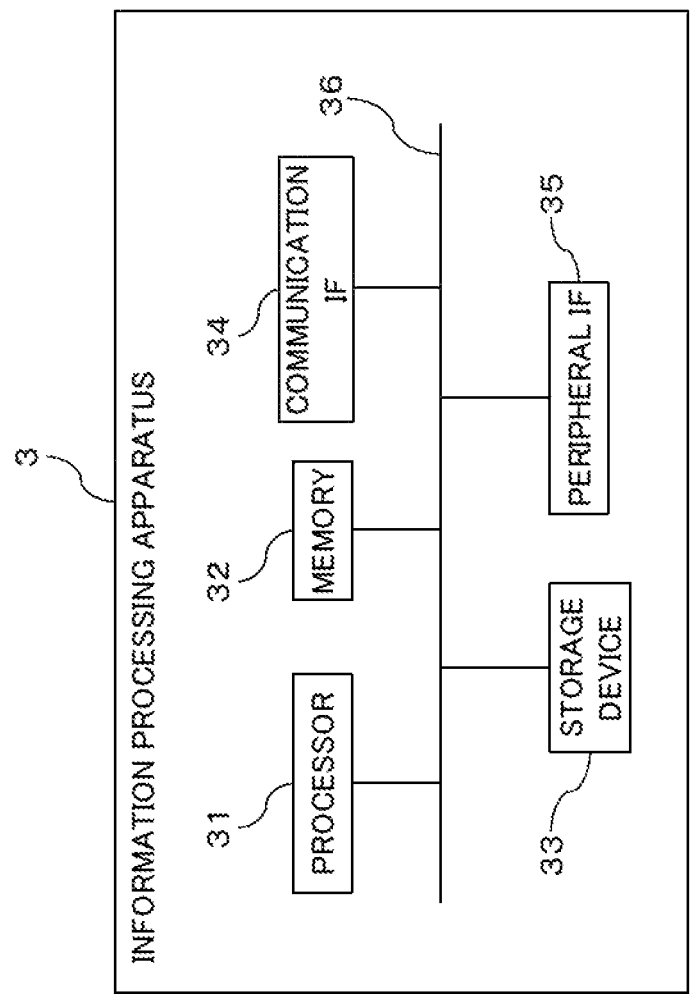
FIG. 4 is a block diagram illustrating a configuration example of an information processing apparatus according to an embodiment.

Next, the configuration example of the information processing apparatus 3 illustrated in FIG. 1 will be described with reference to FIG. 4. As illustrated in FIG. 4, the information processing apparatus 3 may illustratively include the processor 31, a memory 32, a storage device 33, a communication interface (IF) 34 and a peripheral IF 35.

The processor 31, the memory 32, the storage device 33, the communication IF 34 and the peripheral IF 35 may be illustratively connected to a communication bus 36 to communicate with each other through the processor 31.

The processor 31 is an example of an arithmetic processing apparatus which has a capability of arithmetic processing. The arithmetic processing apparatus may be referred to as an arithmetic processing device or an arithmetic processing circuit. An IC such as a CPU or a MPU or a DSP may be illustratively applied to the processor 31 which is an example of the arithmetic processing apparatus. The "processor" may be referred to as a "processing unit", a "controller" or a "computer".

The processor 31 illustratively controls an entire operation of the information processing apparatus 3. The control performed by the processor 31 may include a control for communication performed through the network 4. By controlling the communication, the air conditioner 7 and the luminaire 8 may be remotely controlled through the network 4, for example.

Illustratively, the processor 31 may detect the heartbeat or control the filter characteristics as described above based on the sensor information of the vital sensor 2, which is received by the communication IF 34.

Further, the processor 31 may illustratively generate a control signal to control a spatial environment in which the user of the vital sensor 2 is positioned, such as a control signal to control operations of the air conditioner 7 and the luminaire 8.

The control signal may be illustratively generated based on a heart rate of the user detected based on the sensor information obtained from the vital sensor 2 and a state related to a sleep of the user estimated or determined based on the heart rate.

The control signal generated by the processor 31 may be illustratively transmitted to the air conditioner 7 and the luminaire 8 through the communication IF 34.

The memory 32 is an example of a storage medium, and may be a RAM or a flash memory. A program and data read and used by the processor 31 to operate may be stored in the memory 32.

The storage device 33 may store various pieces of data and programs. A hard disk drive (HDD), a solid state drive (SSD) or a flash memory may be applied to the storage device 33.

The data stored in the storage device 33 may illustratively include the sensor information of the sensor 2 received by the communication IF 34, the heart rate detected based on the sensor information, and the state related to the sleep of the user estimated or determined based on the heart rate.

The data stored in the storage device 33 may be optionally compiled in a database (DB). The data compiled in the DB may be referred to as "cloud data" or "big data". The storage device 33 and the memory 32 may be collectively referred to as a "storage unit" of the information processing apparatus 3.

The programs stored in the storage device 33 may include a program to execute processes described with reference to FIGS. 6 and 12.

The program to execute the processes described below with reference to FIGS. 6 and 12 may be referred to as a "sensor information processing program" for descriptive purposes.

All or part of program codes configuring a program may be stored in the storage unit or may be described as a part of an operating system (OS).

The program and the data may be recorded in a computer-readable non-transitory recording medium to be provided. Examples of the recording medium include flexible disks, CD-ROMs, CD-Rs, CD-RWs, MOs, DVDs, Blu-ray disks and portable hard disks. Further, a semiconductor memory such as a USB (Universal Serial Bus) memory is an example of a recording medium.

Alternatively, the program and the data may be provided (or downloaded) from the server to the information processing apparatus 3 through the network 4. For example, the program and the data may be provided to the information processing apparatus 3 through the communication IF 34. Further, the program and the data may be inputted to the information processing apparatus 3 from an input device described below which is connected to the peripheral IF 35.

The communication IF 34 is an example of a communication unit provided in the information processing apparatus 3, and is illustratively connected to the network 4 to enable communication through the network 4.

Upon focusing on a reception process, the communication IF 34 is an example of a receiver (which may be referred to as an "acquiring unit") which receives information transmitted from the vital sensor 2 to the information processing apparatus 3.

Meanwhile, upon focusing on a transmission process, the communication IF 34 is an example of a transmitter which transmits the control signal generated by the processor 31 to the vital sensor 2, the air conditioner 7 and the luminaire 8, for example. An Ethernet (registered trademark) card may be illustratively applied to the communication IF 34.

The communication IF 34 may be connected with the communication IF 25 of the vital sensor 2 without being routed through the network 4 to enable direct communication with the vital sensor 2.

The peripheral IF 35 is illustratively an interface which connects peripheral devices to the information processing apparatus 3.

The peripheral devices may include an input device which inputs information to the information processing apparatus 3, and an output device which outputs information generated by the information processing apparatus 3.

The input device may include a keyboard, a mouse and/or a touch panel. The output device may include a display and/or a printer.

By the way, when a heartbeat of the user is measured by using the wireless sensor 21 without contacting the user and when a physical motion (may be referred to as a "body motion") of the user becomes large to some extent, for example, it is difficult to detect a heartbeat component from the detected signal of the wireless sensor 21.

For example, during an exercise or an activity of the user, since a motion larger than a motion during rest would be occurred, a distance between the vital sensor 2 and a skin changes according to the body motion.

Illustratively, when the vital sensor 2 is put in a pocket of clothes of the user or when the vital sensor 2 is attached on the clothes of the user with the harness, the distance between the vital sensor 2 and the skin is easy to change according to the body motion.

Hence, a body motion derived signal component corresponding to the change in the distance is added as a noise component to the detected signal of the wireless sensor 21 in addition to a heartbeat derived signal component corresponding to the change in the distance. Hence, as the body motion of the user becomes larger, a noise component for a detection target of the heartbeat component is easily mixed in the detected signal of the wireless sensor 21, and therefore, it is difficult to detect the heartbeat component in the detected signal.

Not only in case of the wireless sensor 21 but also in case of a sensor such as an earclip which optically measures a change in a bloodstream, a bloodstream amount changes due to a body motion. Therefore, in addition to a heartbeat derived signal component, a body motion derived signal component is mixed as a noise component in a sensor detected signal.

Further, when the bloodstream amount changes due to the body motion, a blood pressure changes. Therefore, in a heartbeat sensor which uses a pressure sensor or a piezoelectric sensor, a body motion derived signal component becomes a noise component for a heartbeat derived signal component.

In a sensor such as an electrocardiograph or a phonocardiograph which measures a change in a potential of a heart muscle or a change in sound, since user's muscle moves due to the body motion, a body motion derived signal component becomes a noise component for a heartbeat derived signal component.

In short, independent to a measuring scheme of the heartbeat sensor, in other words, independent to a type of the heartbeat sensor, the signal component corresponding to the body motion is easily mixed as the noise component in a sensor detected signal when a body motion occurs during a user's exercise or activity.

By applying the above-described BPF to a detected signal of the wireless sensor 21, it may be possible to cancel a noise component which is not a heartbeat derived signal component to be detected.

Figure 5:
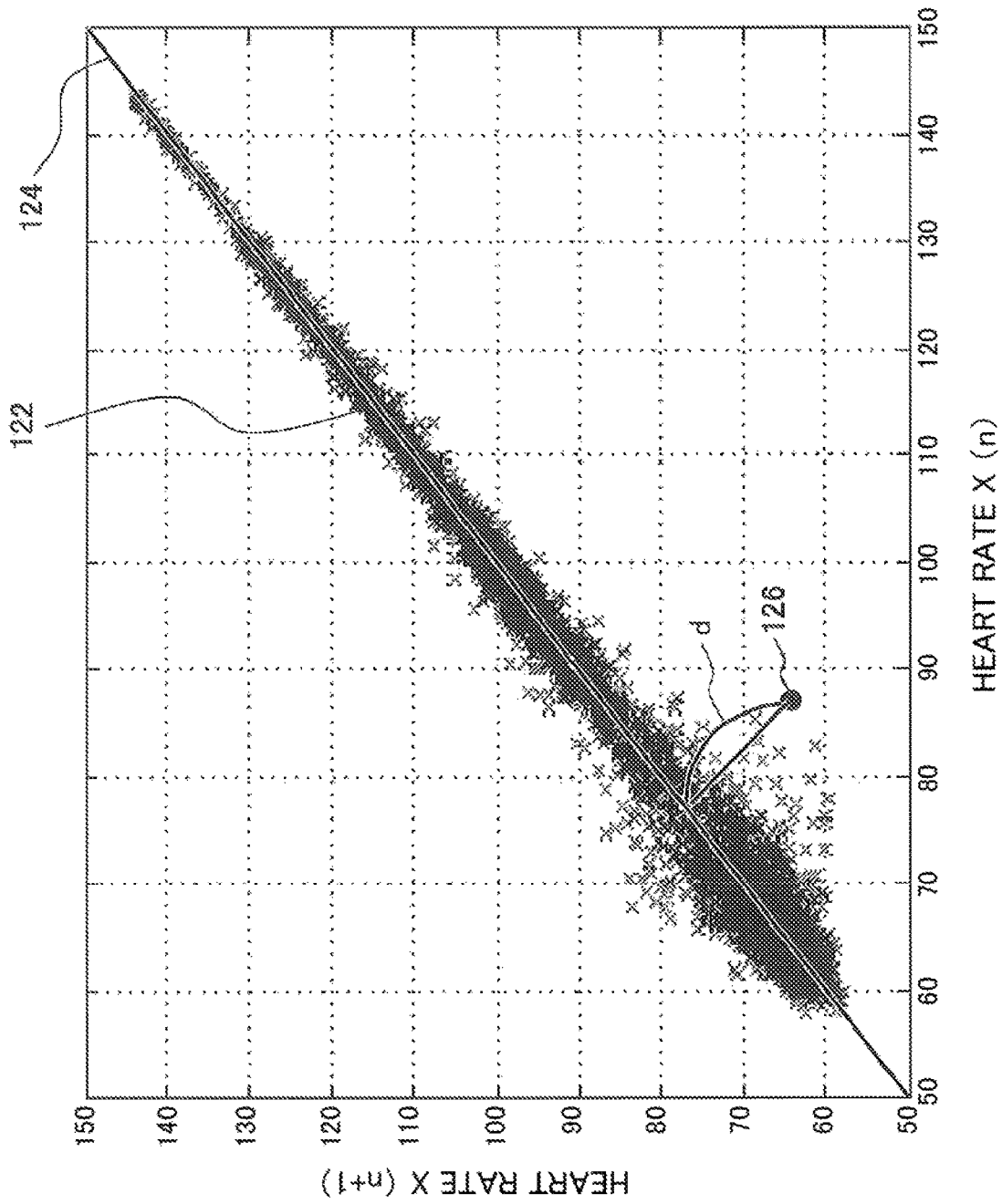
FIG. 5 is a diagram illustrating an example of a result of a heart rate measurement according to an embodiment.

In this regard, as illustrated in FIG. 5, for example, a time length (or a time interval) of a heartbeat per beat tends to vary according to a degree of a heart rate per unit time. In FIG. 5, a horizontal axis indicates a heart rate x(n) (n is a positive integer) at a given timing, and a vertical axis indicates the following heart rate x(n+1). Meanings of reference numerals 122, 124, 126 and "d" in FIG. 5 will be described below.

For example, as the heart rate per unit time increases, a variation of the time length per beat tends to decrease. Conversely, as the heart rate per unit time decreases, a variation of the time length per beat tends to decreases.

Illustratively, in an average frequency band (for a non-restrictive example, 0.8 to 4.0 Hz) in which a heartbeat component is likely to appear, a variation of ±20% possibly occurs in a time length per beat at 50 beats per unit time (e.g. one minute). Meanwhile, a variation of ±5% possibly occurs in a time length per beat at 120 beats higher than the 50 beats. Such a "variation" may be considered as "heartbeat characteristics" of the biological object.

Hence, when the filter characteristics of the BPF (e.g. passband width) is statically set to a specific heart rate such as 60 beats or 120 beats, a heartbeat component may lack or a cancelation of a noise component may be insufficient according to a degree of the heart rate. As a result, a detection accuracy of the heart rate may be decreased.

Hence, in the present embodiment, the filter characteristics of the BPF are adaptively changed according to a degree of the heart rate. For example, as the heart rate per unit time increases, the passband width of the BPF is set to be narrower. Conversely, as the heart rate per unit time decreases, the passband width of the BPF is set to be wider.

An average frequency band in which a heartbeat component is likely to appear will be referred to as a "heartbeat appearance band" for descriptive purposes. A variable setting example of the passband width of the BPF for a heartbeat appearance band will be described below with reference to FIGS. 13 to 22.

According to such variable setting of the passband width of the BPF, it is possible to reduce a missing heartbeat component and improve a cancellation efficiency of a noise component in an average frequency band in which a heartbeat component is likely to appear. The degree of the heart rate can be determined according to a degree of a frequency having a peak value in a result of the frequency analysis on the detected signal of the wireless sensor 21.

However, when a body motion of the user occurs, since a body motion derived signal component becomes large, a probability of erroneous detection becomes high on the ground that a peak value of the body motion derived signal component is easily detected as a peak value of a heartbeat component.

For example, as a change in a distance between the wireless sensor 21 and the user increases, an amplitude of the detected signal detected by the wireless sensor 21 tends to increase. Meanwhile, as a speed of the change in the distance increases, a frequency of the detected signal tends to increase.

Hence, a body motion derived signal component larger than the heartbeat component is easily to appear in the heartbeat appearance band in a result of the frequency analysis on the detected signal of the wireless sensor 21. As a result, a peak value of the body motion derived signal component, in other words, a peak value of a noise component for the heartbeat component to be detected would erroneously be detected as the heartbeat component.

When such erroneous detection occurs, the passband width of the BPF is set based on the frequency of the noise component. Hence, the heartbeat component lacks or a cancelation of the noise component may be insufficient. Therefore, a detection accuracy of the heart rate would decrease.

The decrease in the detection accuracy of the heart rate can be prevented or suppressed by, for example, estimating a heart rate of the user by using means different from the wireless sensor 21 to set and control the filter characteristics of the BPF based on the estimated heart rate.

An example of the different means available to estimate the heart rate of the user is, for example, to estimate the heart rate of the user based on a body motion of the user. The body motion of the user can be detected by the inertial sensor 22.

For example, a change corresponding to a magnitude and a speed of the body motion appears in a detected signal of the inertial sensor 22. As the magnitude of the body motion and the speed of the body motion increase, the exercise intensity of the user increases. Further, as the exercise intensity increase, the heart rate of the user tends to increase.

Therefore, it is possible to estimate the heart rate of the user based on the detected signal of the inertial sensor 22. Hence, in the present embodiment, the heart rate of the user is estimated based on the detected signal of the inertial sensor 22, and the filter characteristics of the BPF applied to the detected signal of the wireless sensor 21 are adaptively controlled according to the estimated heart rate.

Thereby, it is possible to improve a detection accuracy of a heartbeat signal in the heartbeat appearance band. Consequently, even in a situation that a body motion derived noise component appears more in a detected signal of the wireless sensor 21 during an exercise or an activity of the user than during a rest time, it is possible to accurately measure the heart rate of the user.

since a measurement accuracy of the heart rate of the user is improved, it is also possible to improve an accuracy and efficiency to control a spatial environment in which the user is positioned, for example.

(Operation Example)

Some operation examples of the sensor system 1 according to the present embodiment will be described. In an example described below, a wireless sensor value and an inertial sensor value of the vital sensor 2 are processed by the information processing apparatus 3. However, the same process described below may be performed by the vital sensor 2 (e.g. processor 23).

FIRST EXAMPLE

Figure 6:
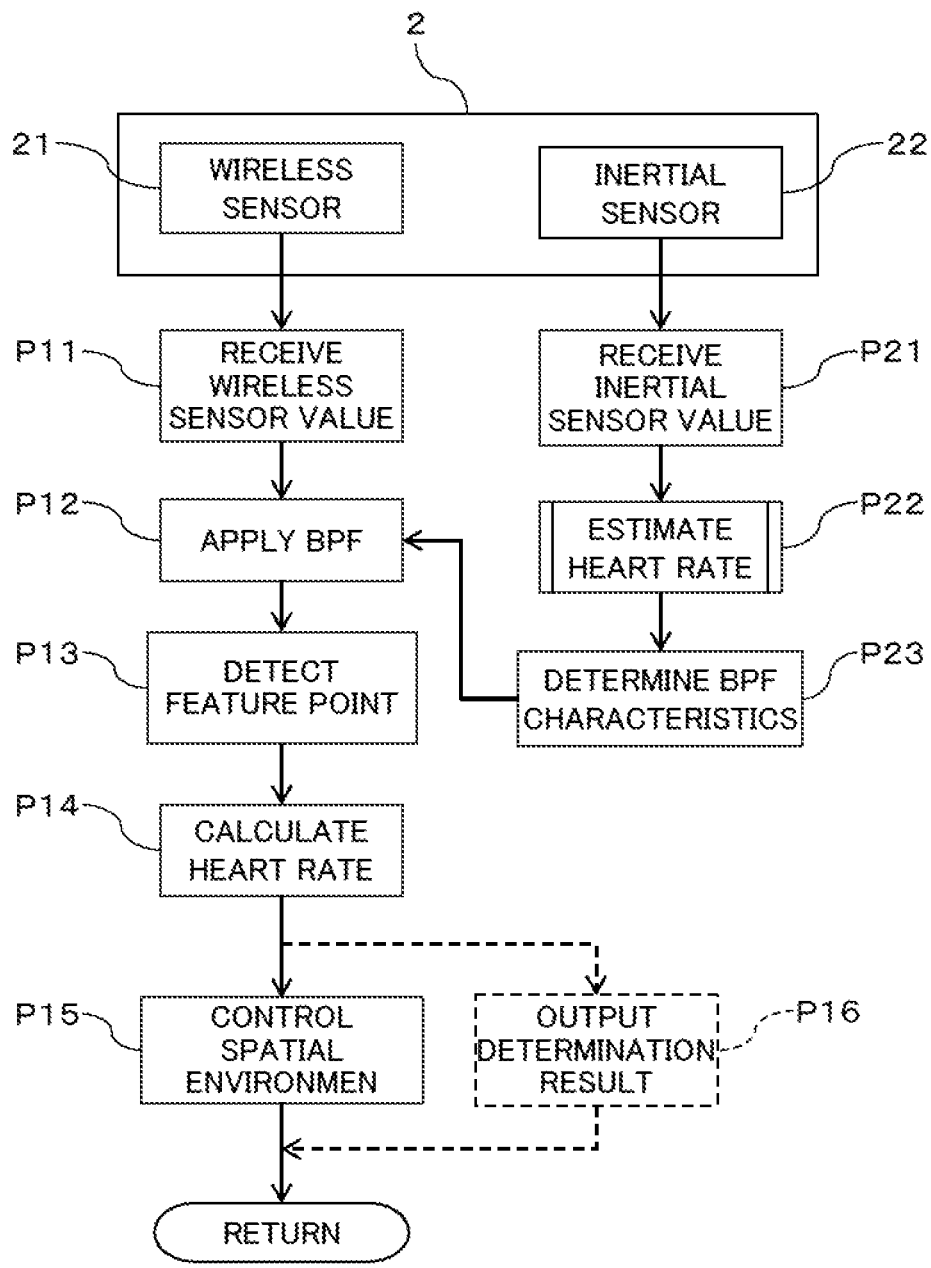
FIG. 6 is a flowchart illustrating an operation example of the sensor system according to a first embodiment.

FIG. 6 is a flowchart illustrating an operation example of the sensor system 1 according to a first example. As illustrated in FIG. 6, the information processing apparatus 3 receives a wireless sensor value and an inertial sensor value from a sensor unit 2 (processes P11 and P21).

Figure 7:
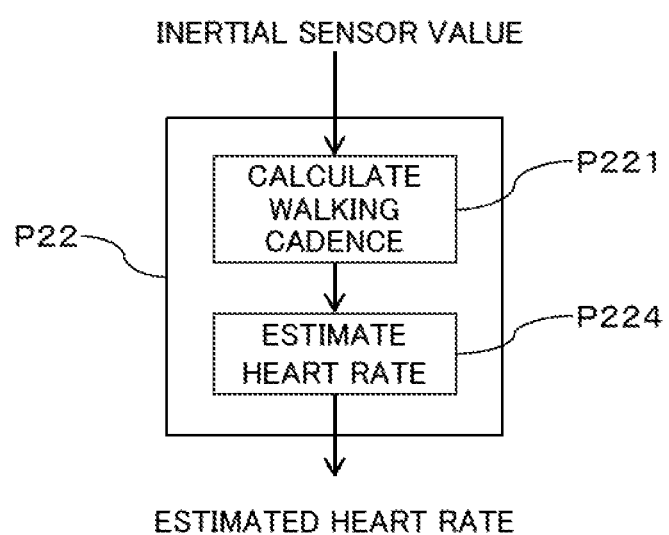
FIG. 7 is a flowchart illustrating a first example of a heart rate estimation process illustrated in FIG. 6.
Figure 8:
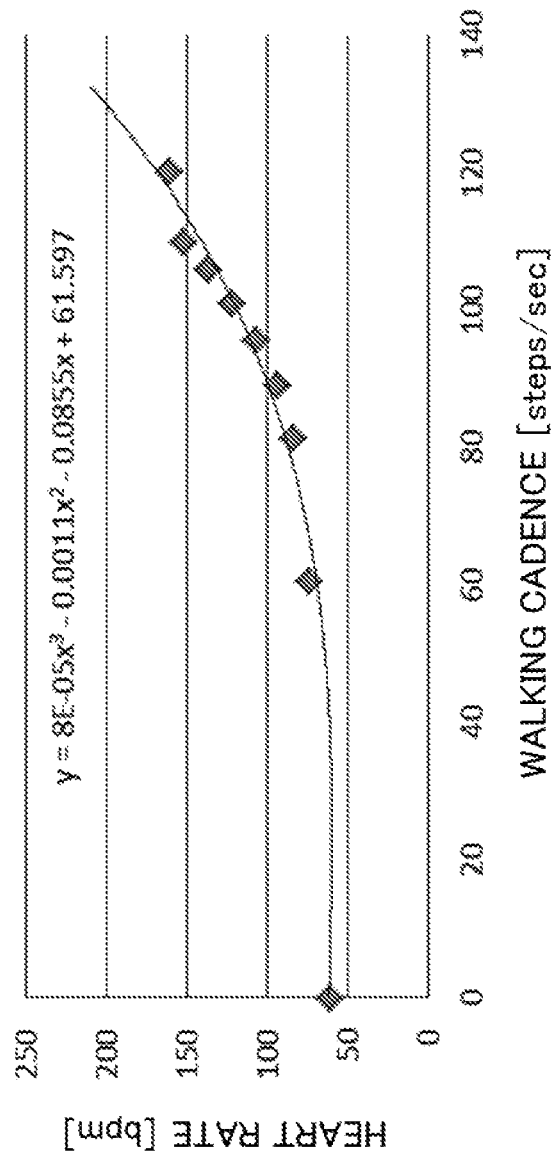
FIG. 8 is a diagram illustrating an example of a relationship between a walking cadence and a heart rate according to one embodiment.
Figure 9:
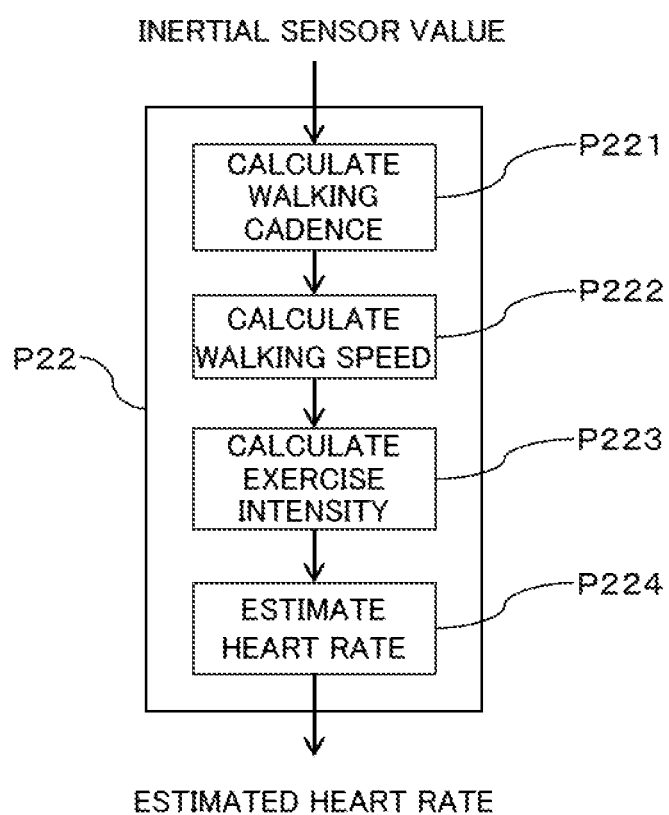
FIG. 9 is a flowchart illustrating a second aspect of a heart rate estimation process illustrated in FIG. 6.
Figure 10:
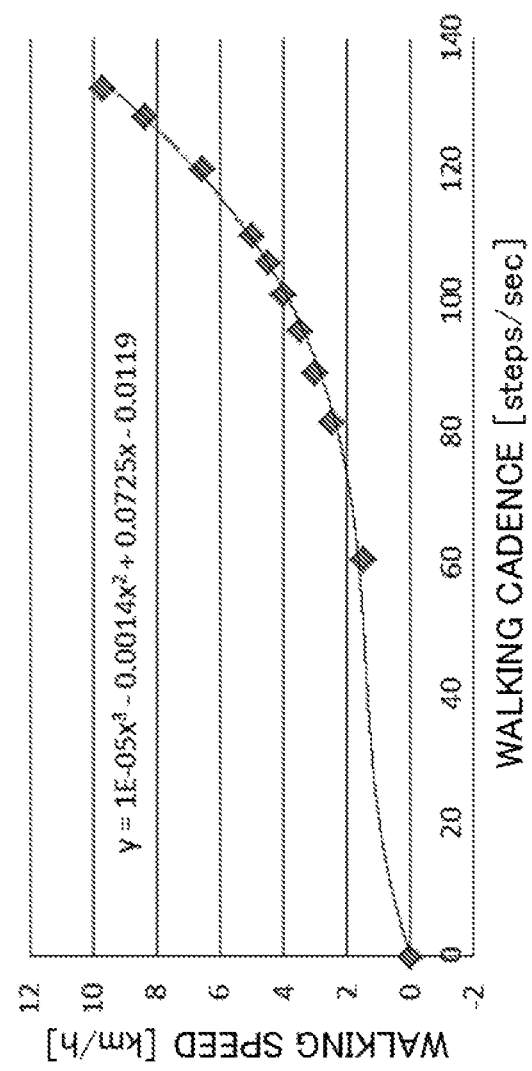
FIG. 10 is a diagram illustrating an example of a relationship between a walking cadence and a walking speed according to one embodiment.

For example, the processor 31 of the information processing apparatus 3 estimates a heart rate of a user based on the inertial sensor value in response to a reception of the inertial sensor value (process P22). FIGS. 7 and 8 illustrate a first aspect of a heart rate estimation process, and FIGS. 9 to 11 illustrate a second aspect of a heart rate estimation process.

(First Aspect of Heart Rate Estimation Process)

As illustrated in FIG. 7, the processor 31 may calculate the number of steps (which may be referred to as a "walking cadence") of the user per unit time (for example, during one second) based on an inertial sensor value (process P221). Similar to general pedometers, the number of steps can be obtained by, for example, counting in the processor 31 the number of times that the inertial sensor value exceeds a threshold value.

Here, the walking cadence and the heart rate can be linked by a relational equation. The relational equation may be illustratively derived by performing a curve-fitting on a plurality of actual measured values, for example.

A non-restrictive example of the relational equation of the walking cadence and the heart rate can be expressed by following polynominal equation (1) as illustrated in FIG. 8.

$$y=8E-05x^3-0.0011x^2-0.0855x+61.597 \tag{1}$$

In FIG. 8, a horizontal axis "x" indicates a walking cadence [the number of steps/second], and a vertical axis "y" indicates a heart rate per unit time (for example, one minute) [beats per minute, bpm]. Further, "8E–05" represents "$8 \times 10^{-5}$".

The processor 31 may calculate a heart rate by calculating equation (1) based on the walking cadence calculated in process P221 (process P224 in FIG. 7). The calculated heart rate may be referred to as an "estimated heart rate" for descriptive purposes.

The relation illustrated in FIG. 8 may be expressed by data in a table format (which may be referred to as "table data"), for example. The table data may be stored in a memory 32 or a storage device 33 (see FIG. 4) of the information processing apparatus 3, for example. The processor 31 may determine an estimated heart rate for the walking cadence with reference to the table data without performing arithmetic processing.

(Second Aspect of Heart Rate Estimation Process)

Next, a second aspect of the heart rate estimation process (P22) in FIG. 6 will be described with reference to FIGS. 9 to 11. In the above-described first aspect, a heart rate is calculated based on a walking cadence of the user. In contrast, a heart rate may be calculated based on an exercise intensity of the user in the second aspect.

As illustrated in FIG. 9, the processor 31 may calculate the walking cadence of the user based on the wireless sensor value (process P221) in a manner similar to the first aspect (see FIG. 7).

The processor 31 may calculate a walking speed based on the walking cadence according to the calculated walking cadence (process P222).

In this regard, the walking cadence and the walking speed can be linked by a relational equation. The relational equation may be derived by performing a curve-fitting on a plurality of actual measured values.

A non-restrictive example of the relational equation of the walking cadence and the walking speed can be expressed by following polynominal equation (2) as illustrated in FIG. 10.

$$y = 1E{-}05x^3 - 0.0014x^2 + 0.0725x - 0.0119 \quad (2)$$

In FIG. 10, a horizontal axis "x" indicates a walking cadence [the number of steps/second], and a vertical axis "y" indicates a walking speed [km/h] per unit time (illustratively, one hour). Further, "1E−05" represents "1×10$^5$".

As a walking distance per unit time increases, a step width of a distance per step and the number of steps also tend to increase. For example, a step width=height×0.37 is applicable when the user walks 70 m per minute (=4.2 km per hour), a step width=height×0.45 is applicable when the user walks 90 m per minute (=5.4 km per hour) and a step width=height×0.5 is applicable when the user walks 110 m per minute (=6.6 km per hour). Therefore, it is possible to approximately calculate the walking speed corresponding to a walking distance per unit time based on the above step width and walking cadence.

The processor 31 may calculate the walking speed by calculating equation (2) based on the walking cadence calculated in process P221.

The relation illustrated in FIG. 10 may be expressed by table data similar to the relation illustrated in FIG. 8 and may be stored in the memory 32 or the storage device 33 (see FIG. 4), for example. The processor 31 may determine a walking speed rate for the walking cadence with reference to the table data without performing arithmetic processing.

In response to the calculation of the walking speed, the processor 31 may calculate an exercise intensity of the user based on the calculated walking speed (process P223 in FIG. 9). The exercise intensity is an index value indicative of an activity amount of a person, and may be expressed by a METs value.

METs is an abbreviation of "Metabolic equivalents". The METs value may be a numerical value which expresses a relative value (e.g. a multiple number) of a metabolic rate (or a calorie consumption amount) during an activity of a person with respect to a metabolic rate during rest. A table in which METs values are associated with each activity of a person is referred to as a "METs table". The METs table is published by the National Institute of Health and Nutrition, for example.

FIG. 11 illustrates an example of a relation between walking speeds and METs values. A walking speed=0 [km/h] is associated with a METs value=1 and corresponds to a reference exercise intensity during rest. As illustrated in FIG. 11, as the walking speed increases, the METs value also increases.

For example, in case of a walking speed=2.5 [km/h], the METs value is three times as a reference METs value (=1). In case of a walking speed=4 [km/h], the METs value is five times as the reference METs value.

When the METs value is determined, a current heart rate can be determined based on an age of the user and the heart rate during rest, for example. The METs value can be expressed by following equation (3), for example.

$$\text{METs value} = (\text{heart rate} - \text{heart rate during rest})/ \\ (\text{maximum heart rate} - \text{heart rate during rest}) \times 10 \quad (3)$$

The "maximum heart rate" in equation (3) can be calculated as a simplified equation of "220−age".

Therefore, the processor 31 can calculate the current heart rate based on the METs value by calculating equation (3) (process P224 in FIG. 9). In other words, even when it is difficult to accurately detect a heart rate during an exercise or an activity of the user, it is possible to estimate a heart rate based on the METs value by calculating equation (3).

When the estimated heart rate is calculated by the first aspect or the second aspect of the above-described heart rate estimation process, the processor 31 may determine the filter characteristics of the BPF to be applied to a wireless sensor value corresponding to the estimated heart rate, as illustrated in FIG. 6 (process P23). Hereinafter, the filter characteristics of the BPF may be abbreviated as "BPF characteristics".

The processor 31 may convert the estimated heart rate into a frequency and set the converted frequency to a center frequency of the BPF to be applied to the wireless sensor value, for example. The heart rate can be converted into the frequency by dividing the heart rate by 60 (seconds), for example. Further, the processor 31 may set a narrower bandwidth to the BPF when the estimated heart rate is higher. A detailed determination example of the BPF characteristics will be described below.

The processor 31 may apply the BPF having the determined BPF characteristics to the wireless sensor value received in process P11 to filter the wireless sensor value (process P12). According to the filtering, the body motion derived noise component is removed from the wireless sensor value.

The processor 31 may detect a heartbeat component indicative of a distinctive change corresponding to a heartbeat as a "feature point" from the filtered wireless sensor value (process P13). The "feature point" may be, for example, a point at which a first derivation becomes zero in a signal waveform of the filtered wireless sensor value.

In response to detection of the "feature point", the processor 31 can calculate a heart rate per minute by calculating a time interval (e.g. "second") at the feature point and dividing one minute (=60 seconds) by the calculated time interval (process P14).

The calculated heart rate may be used as a parameter to control a spatial environment in which the user of the vital sensor 2 is positioned (process P15). Further, the calculated heart rate may be optionally outputted to an output device such as a display or a printer as indicated by a dotted line in FIG. 6 (process P16).

Information of the BPF characteristics determined in process P23 and information of the feature point detected in process P13 may be optionally outputted to the output device such as the display or the printer. In this case, it is possible to check whether or not a setting status and settings of the BPF characteristics are appropriate, for example.

As described above, according to the first embodiment, the BPF characteristics applied to a wireless sensor value are controlled according to a frequency associated with a heart rate estimated based on an inertial sensor value. Consequently, it is possible to efficiently cancel the noise component appearing in a heartbeat appearance band.

Accordingly, it is possible to improve a detection accuracy of a heartbeat signal based on the wireless sensor value. For example, it is possible to improve a detection accuracy of a heartbeat signal in a band of 1.5 to 4.0 Hz which is considered as being easily influenced by a body motion derived noise component within a band of 0.8 to 4.0 Hz which is an example of the heartbeat appearance band.

SECOND EXAMPLE

In the first example, the BPF characteristics are determined based on an estimated heart rate without depending on a degree of a heart rate estimated based on an inertial sensor value. However, the BPF characteristics may be determined based on a wireless sensor value without depending on the inertial sensor value in accordance with an estimated heart rate.

For example, when a heart rate estimated based on the inertial sensor value is high, a METs value which is an index of an exercise intensity corresponding to the estimated heart rate also tends to be high. Therefore, when the estimated heart rate or the METs value is equal to or more than a threshold value, the BPF characteristics may be determined based on the heart rate estimated based on the inertial sensor value as in the first example.

When the estimated heart rate is higher, in other words, when the METs value is higher, it may be considered that a body motion derived noise component would easily be mixed in a heartbeat appearance band of the wireless sensor value.

In contrast, when the heart rate or the METs value estimated based on the inertial sensor value is less than the threshold value, even though the BPF characteristics are determined based on the wireless sensor value, the body motion derived noise component may be removed sufficiently.

In other words, when the heart rate or the METs value estimated based on the inertial sensor value is less than the threshold value, it may be considered that an impact on detection of a heartbeat component caused by the body motion derived noise component would be a little.

Figure 12:
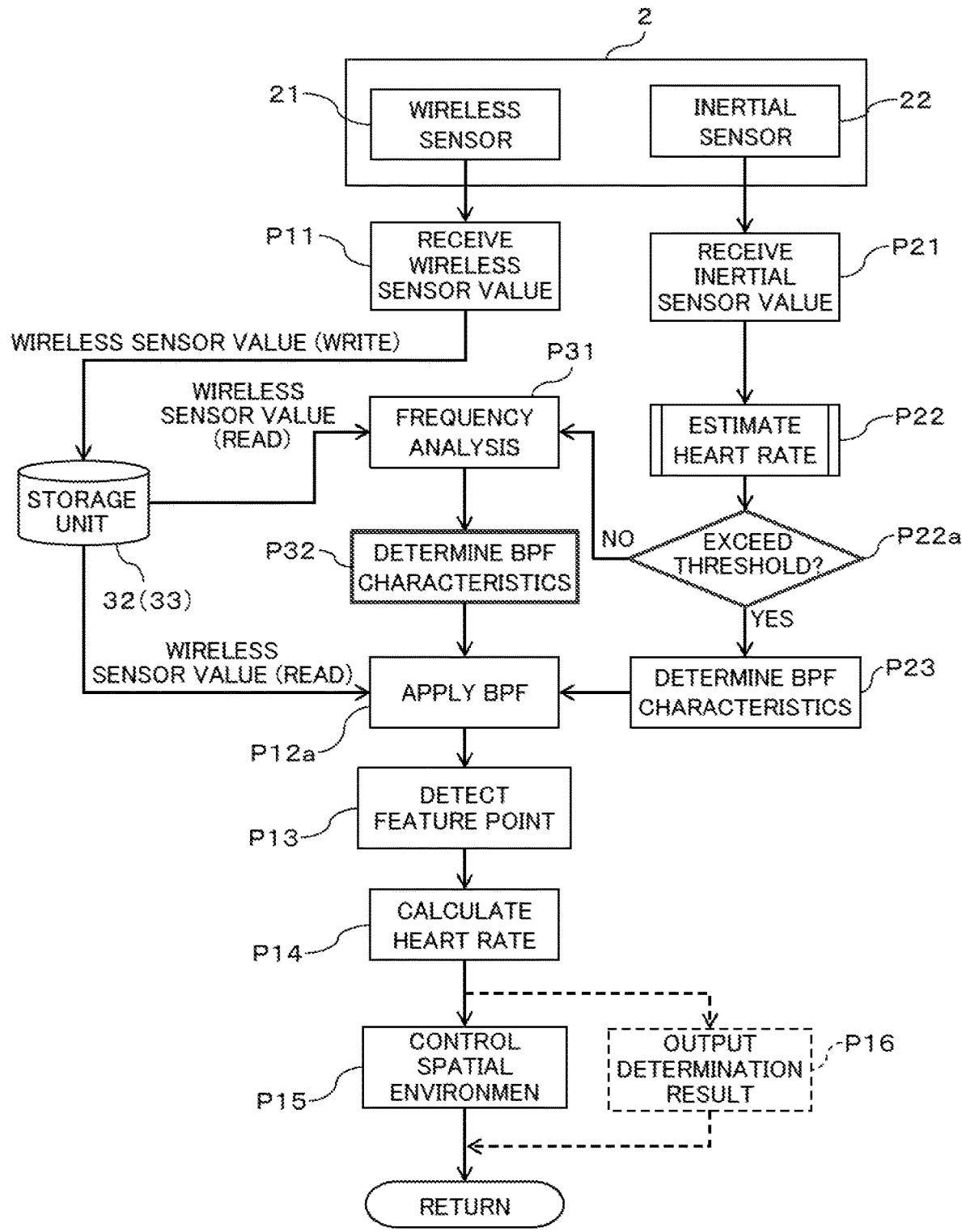
FIG. 12 is a flowchart illustrating an operation example of a sensor system according to a second embodiment.

Hence, in the second example, as illustrated in FIG. 12, which one of the inertial sensor value and the wireless sensor value is to be used for determining the BPF characteristics may be controlled according to a determination with threshold value (process P22a) for the estimated heart rate (or the METs value).

For example, when the estimated heart rate (or METs value) is equal to or more than the threshold value (YES in process P22a), the processor 31 of the information processing apparatus 3 may determine the BPF characteristics based on a frequency corresponding to the heart rate estimated based on the inertial sensor value in a manner similar to the first example (process P23). The frequency corresponding to the heart rate may be referred to as a "heartbeat frequency" for descriptive purposes.

Meanwhile, when the estimated heart rate (or METs value) is less than the threshold value (NO in process P22a), the processor 31 may detect the heart rate based on the wireless sensor value, and determine the BPF characteristics based on a detected heartbeat frequency (processes P31 and P32).

A frequency analysis (process P31) may be used to detect the heart rate from the wireless sensor value. A fast Fourier transform (FFT) or a discrete Fourier transform (DFT) is applicable to the frequency analysis.

The wireless sensor value is converted from a time domain signal into a frequency domain signal (which may be referred to as a "frequency signal" for descriptive purposes) by the FFT or the DFT.

The processor 31 may detect a frequency having a peak value (such frequency may be referred to as a "peak frequency") in the frequency signal of the wireless sensor value as a "feature point" described above, for example. The peak frequency is an example of a frequency component indicative of a distinctive change corresponding to a heartbeat.

The processor 31 may determine the BPF characteristics based on the detected peak frequency (process P32). For example, the processor 31 may determine BPF characteristics having the peak frequency at the center frequency and a narrower bandwidth when the peak frequency is higher (or a wider bandwidth when the peak frequency is lower) as the BPF characteristics to be applied to the wireless sensor value.

The wireless sensor value received by the information processing apparatus 3 in process P11 may be stored in a memory 32 or a storage device 33 in preparation for the above frequency analysis process (P31). The wireless sensor value stored in the memory 32 or the storage device 33 may be read by the processor 31 in process P12a, and a BPF having the BPF characteristics determined in process P23 or P32 may be applied to the wireless sensor value.

A feature point detection process (P13), a heart rate calculation process (P14), a spatial environment control (P15) and a determination result output (P16) performed by the processor 31 after process 12a may be the same as those in the first example.

As described above, according to the second example, the same function and effect as those in the first example are obtained. Additionally, the BPF characteristics are controlled based on the wireless sensor value when the inertial sensor value indicates that an impact on detection of a heartbeat component due to a body motion derived noise component may be considered as being a little.

Accordingly, it is possible to improve a detection accuracy of a heartbeat signal in a band of 0.8 to 1.5 Hz in which the impact due to the body motion derived noise component may be considered as being a little within a band of 0.8 to 4.0 Hz which is an example of the heartbeat appearance band.

(Determination Example of BPF Characteristics)

Next, a detailed example of a process (e.g. process P23 in FIGS. 6 and 12 and process P12a in FIG. 12) to determine (or set) the above-described BPF characteristics will be described with reference to FIGS. 5 and 13 to 22.

A determination example of the BPF characteristics described below may be common to the aforementioned first and second examples. However, in the following description, a "reference heart rate" corresponds to a heart rate estimated based on the inertial sensor value in the first example, and corresponds to a heart rate estimated based on the inertial sensor value or the wireless sensor value in the second example.

For example, in the second example, the "reference heart rate" when YES is determined in threshold determination process P22a in FIG. 12 corresponds to the heart rate estimated based on the inertial sensor value. Meanwhile, the "reference heart rate" when NO is determined in process P22a corresponds to the heart rate detected based on the wireless sensor value.

As described above, FIG. 5 illustrates a relation between a heart rate per unit time and a variation of a time length per heartbeat. Reference numeral 122 denotes measured data (x(n), x(n+1)) of the heart rate and a straight line 124 indicates a median value of each measured data 122.

The straight line indicating the median value 124 is illustratively a straight line of each measured data 122 calculated according to a least-squares method, for example, and is assumed to be expressed as ax(n)+bx(n+1)+c=0. In this regard, coefficients a, b and c are actual numbers.

Here, a length d of a perpendicular line drawn from each measured data 122 (x(n), x(n+1)) to the straight line 124 can be expressed by following equation (4).

$$d = \frac{|ax(n) + bx(n+1) + c|}{\sqrt{a^2 + b^2}} \qquad (4)$$

A measured point having a maximum value of the length d is assumed to be a maximum distance point 126 expressed by a coordinate (x(m), x(m+1)). The "m" represents an positive integer which satisfies m≤n.

A straight line which passes through the maximum distance point 126 and a coordinate (a coordinate (120,114) in the example in FIG. 5) corresponding to "−0.1 Hz" in case of heartbeat frequency=2 Hz represents a lower limit of a bandwidth, for example.

The straight line indicative of an upper limit of the bandwidth corresponds to a straight line which passes through a point (120, 126) and a point having the same width as that of the lower limit of a bandwidth at any of frequencies, for example. A bandwidth in case of heartbeat frequency=2 Hz may be determined with reference to a maximum value and a minimum value of a next heartbeat at heart rate x(n)=120 of the measured data 122 in FIG. 5.

Figure 13:
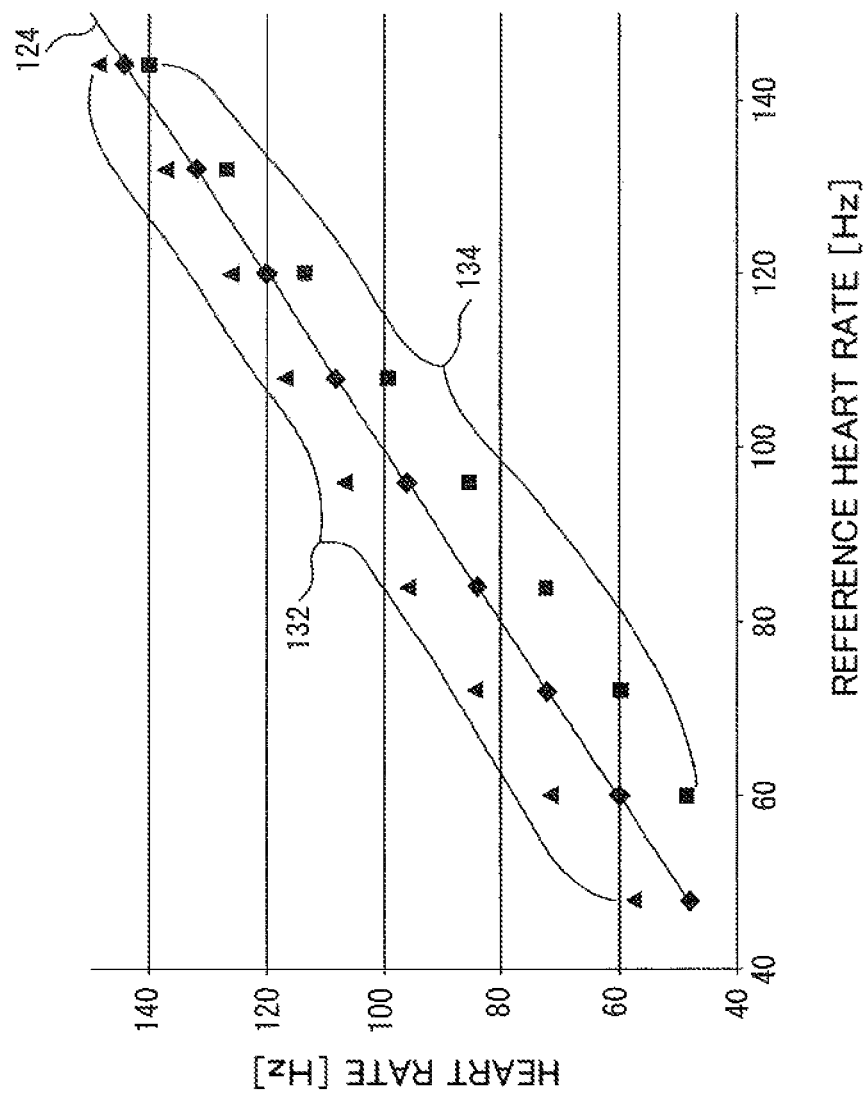
FIG. 13 is a diagram illustrating a setting example of a BPF according to one embodiment.

Next, FIG. 13 is a diagram illustrating a setting example of the BPF characteristics. FIG. 13 illustrates an example of an upper limit and a lower limit of a band of the BPF calculated by substituting the reference heart rate in a preset equation.

In FIG. 13, a horizontal axis indicates a reference heart rate [Hz], and a vertical axis indicates a heart rate [Hz] corresponding to an upper limit and a lower limit of a bandwidth. In FIG. 13, the upper limit of the bandwidth is indicated by a band upper limit value 132, and the lower limit of the bandwidth is indicated by a band lower limit value 134. FIG. 13 illustrates the upper limit values and the lower limit values of the bandwidth at some reference heart rate.

The above "preset equation" may be determined by interpolation or extrapolation based on, for example, the maximum distance point 126 and reference coordinates (120, 126) and (120, 114) determined based on the measured data 122 illustrated in FIG. 5.

Figure 14:
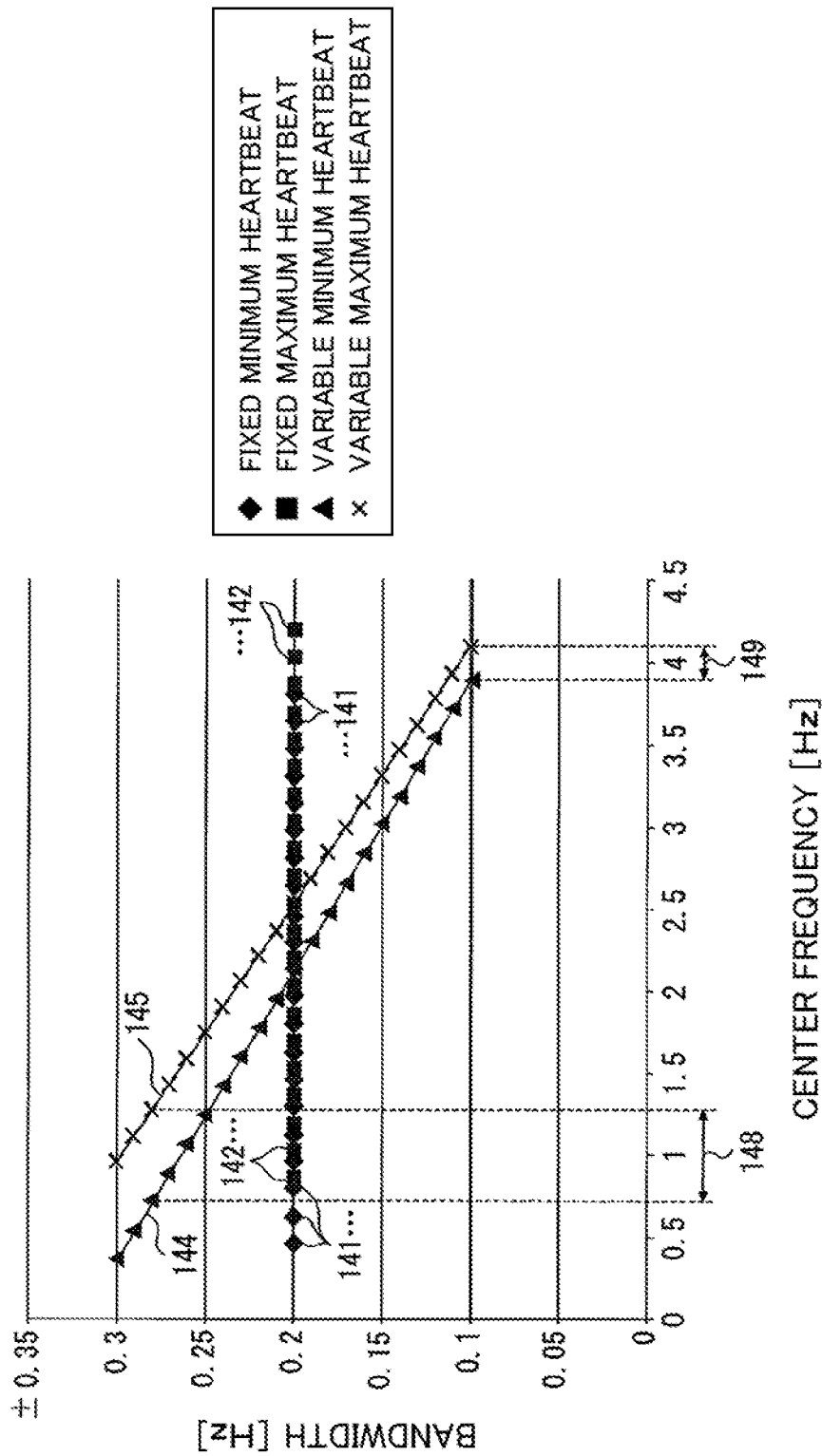
FIG. 14 is a diagram illustrating an example of a passband of the BPF according to one embodiment.

Next, FIG. 14 is a diagram illustrating an example of a passband of the BPF. In FIG. 14, a horizontal axis indicates a center frequency of the BPF, and a vertical axis indicates a bandwidth of the BPF. Further, in FIG. 14, a fixed minimum heartbeat 141 or a variable minimum heartbeat 144 indicates a heart rate corresponding to a lower limit of a band when a bandwidth corresponding to a given center frequency is adopted.

Furthermore, in FIG. 14, a fixed maximum heartbeat 142 or a variable maximum heartbeat 145 indicates a heart rate corresponding to a lower limit of a band when a bandwidth corresponding to a given center frequency is adopted.

The fixed minimum heartbeat 141 and the fixed maximum heartbeat 142 are comparative examples in case where a bandwidth does not change according to a heart rate in comparison with a case where the bandwidth of the BPF is variable in the present embodiment.

According to the variable minimum heartbeat 144 and the variable maximum heartbeat 145, the bandwidth of the BPF corresponds to a bandwidth indicated by reference numeral 148 near heart rate=1 Hz and corresponds to a bandwidth indicated by reference numeral 149 which is narrower than the bandwidth 148 near heart rate=4 Hz, for example. Thus, the wider bandwidth 148 is set at a lower heart rate, and the narrower bandwidth 149 is set at a higher heart rate.

Figure 15:
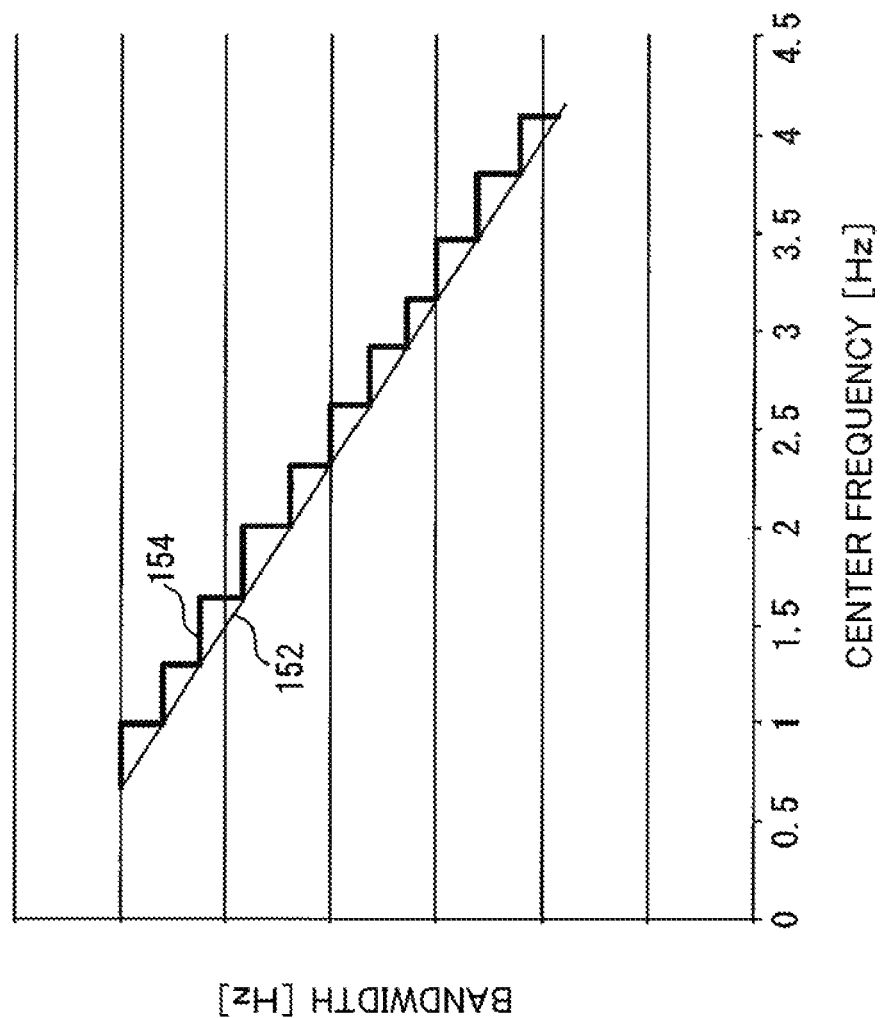
FIG. 15 is a diagram illustrating a setting example of a bandwidth of a BPF according to one embodiment.

FIG. 15 is a diagram illustrating a setting example of the BPF bandwidth. In FIG. 15, a horizontal axis indicates a center frequency, and a vertical axis indicates a bandwidth. In FIG. 15, a straight line 152 indicates an example of a setting value of a bandwidth with respect to the center frequency. For example, in examples described with reference to FIGS. 5 and 14, the bandwidth 152 may be set to decrease linearly in response to an increase of the center frequency.

A relation between the center frequency and the bandwidth may be enough to have a relation in which the bandwidth becomes wider when the center frequency becomes lower, and does not need to be a relation expressed by a straight line. For example, as indicated by reference numeral 154 in FIG. 15, the bandwidth may be set such that the bandwidth changes stepwise with respect to the center frequency. The relation between the bandwidth and the center frequency may be determined by interpolation and extrapolation using one or more suitable functions of a monotonic increase based on given two or more points determined based on an actual measured value, for example.

Figure 16:
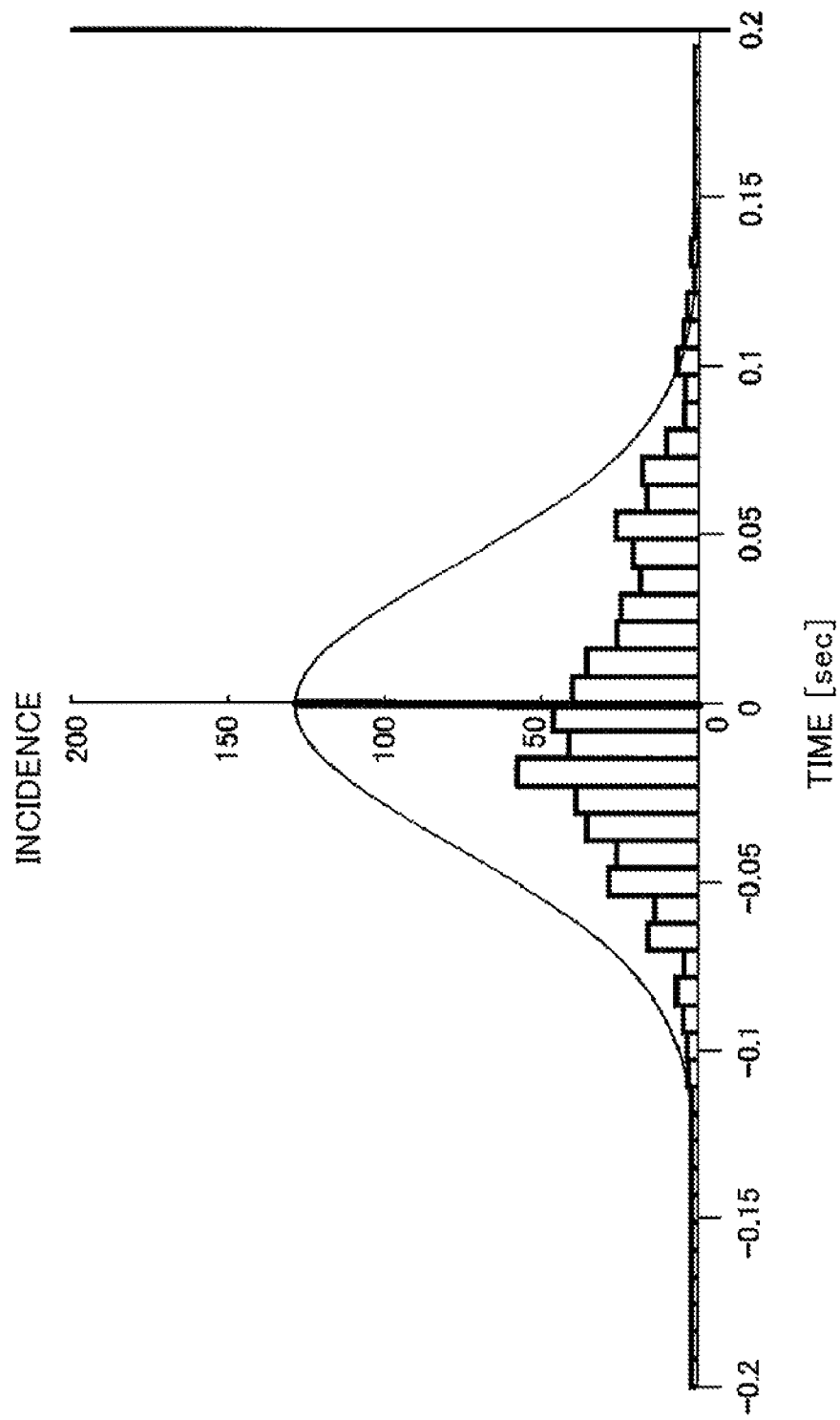
FIGS. 16 and 17 are diagrams illustrating examples of distributions of the heart rate according to an embodiment.
Figure 17:
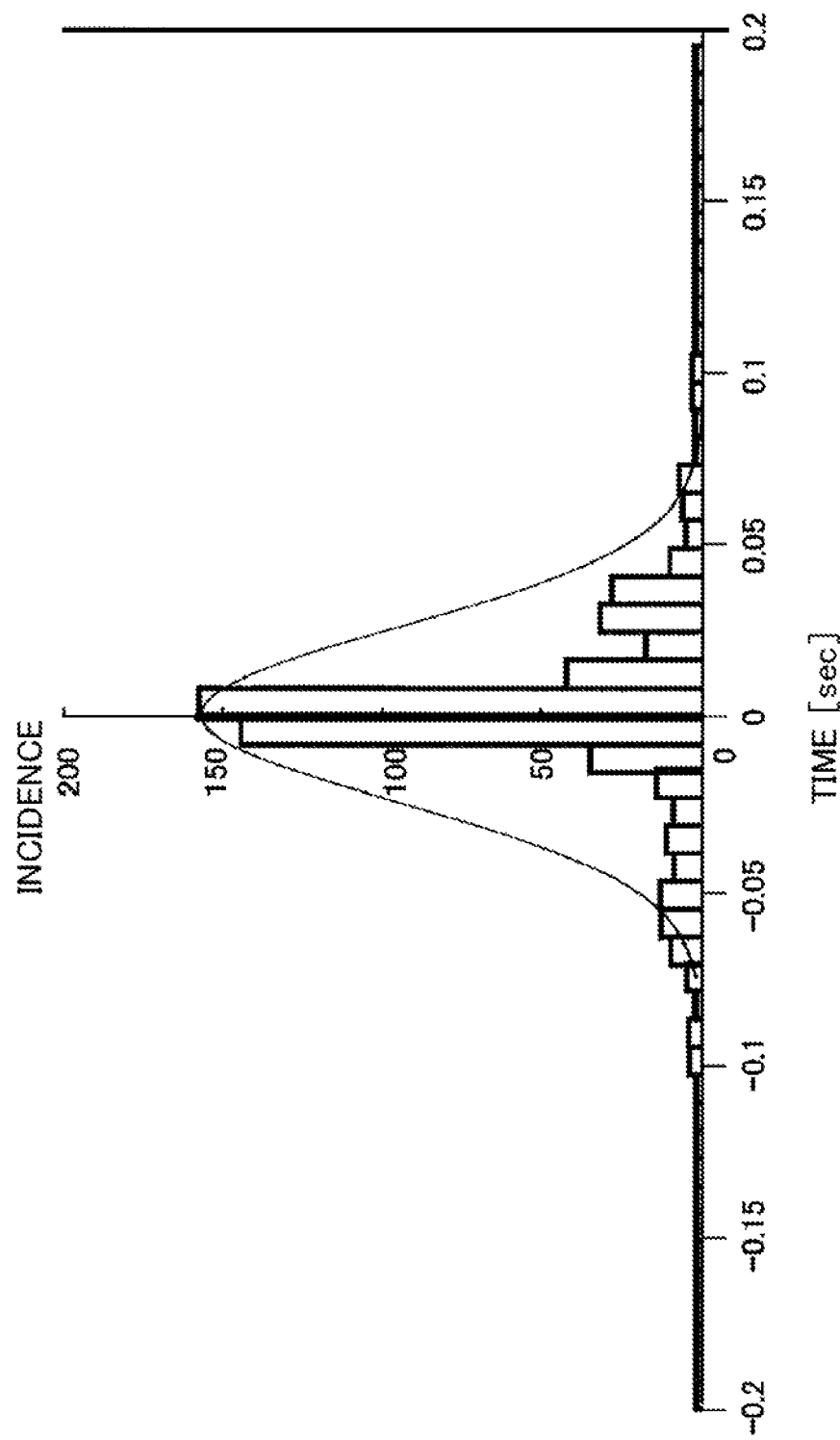

Next, FIGS. 16 to 19 are diagrams illustrating other setting examples of bandwidths. FIGS. 16 and 17 are diagrams illustrating examples of a heart rate distribution, and FIGS. 18 and 19 are diagrams illustrating examples of a heart rate statistical process. In FIGS. 16 and 17, horizontal axes indicate a time indicative of a difference between a heartbeat interval at a given point of time and a next heartbeat interval, and vertical axes indicate the number of measured times.

FIG. 16 illustrates a heart rate distribution whose heart rate is near 55 to 60, and FIG. 17 illustrates a heart rate distribution whose heart rate is near 75 to 80. In comparison between FIGS. 16 and 17, items of measured data concentrate more near the vertical axis at the heart rate near 55 to 60 than at the heart rate near 75 to 80, and the heart rate varies less. The measured data used for a statistical process may be data measured by an electrocardiograph which measures a heartbeat by placing an electrode in contact with a biological object, for example.

FIGS. 18 and 19 illustrate examples of the statistical process of actual measured data at the heart rate near 60 and at the heart rate near 120. In examples of the statistical process illustrated in FIGS. 18 and 19, a probability distribution of 532 items of data is calculated, and the bandwidth of the BPF is calculated such that the measured data is in a range of a certain probability or more.

In the example of the statistical process in FIG. 18, by determining a range of 8σ of the calculated probability distribution and CP value=1.33 at the heart rate near 60, the bandwidth is ±0.165 Hz. Here, σ represents a standard deviation, and "CP" represents "Process Capability". The same bandwidth as this bandwidth at the heart rate near 120 is provided in case of CP value=2.16.

Similarly, in the example of the statistical process in FIG. 19, by determining a range of 8σ of the calculated probability distribution and CP value=1.33 at the heart rate near 120, the bandwidth is ±0.1015 Hz. The same bandwidth as this bandwidth at the heart rate near 60 is provided in case of CP value=0.82.

The statistical process of an actual measured value is performed as described above, and the bandwidth of the BPF which enables data detection at a given probability or more is set. In this case, the relation between the bandwidth and the center frequency corresponding to the reference heart rate may be linearly determined based on given two points or may be determined by interpolation by performing the above statistical process on the center frequency of a shorter interval.

Alternatively, the relation between the bandwidth and the center frequency may be determined by interpolation and extrapolation by using one or more suitable functions of a monotonic increase based on each point when the given two or more points are determined, or may be set such that the bandwidth changes stepwise with respect to the center frequency.

Figure 20:
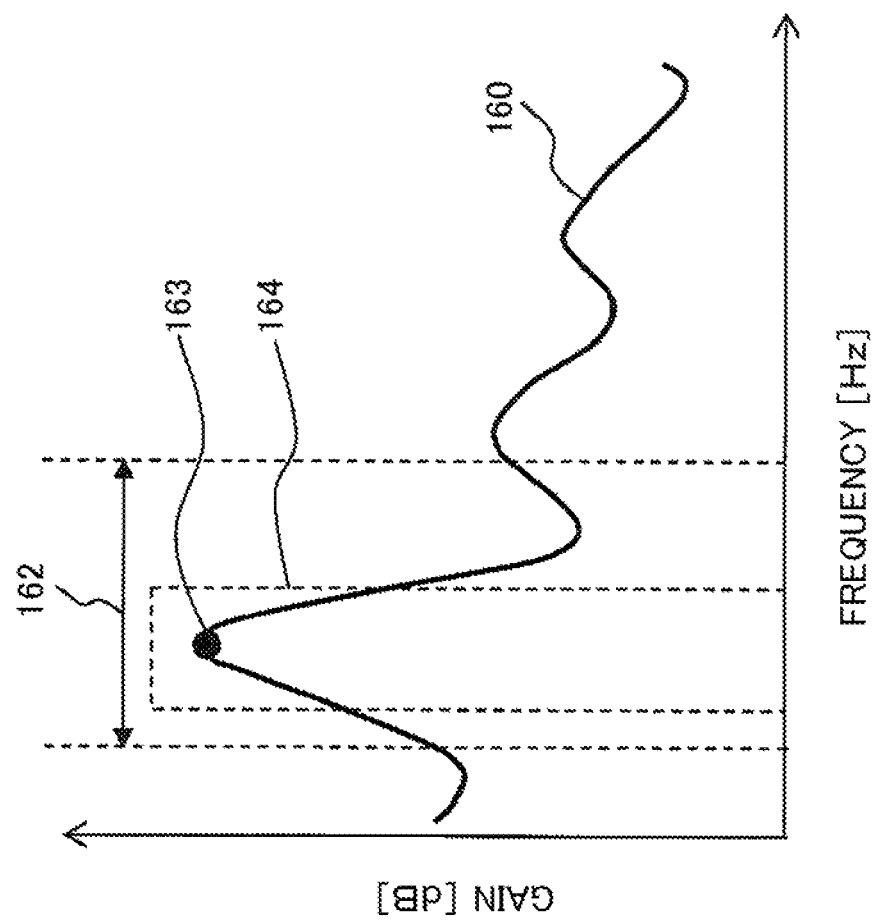
FIGS. 20 and 21 are diagrams illustrating setting examples of a bandwidth of a BPF according to one embodiment.
Figure 21:
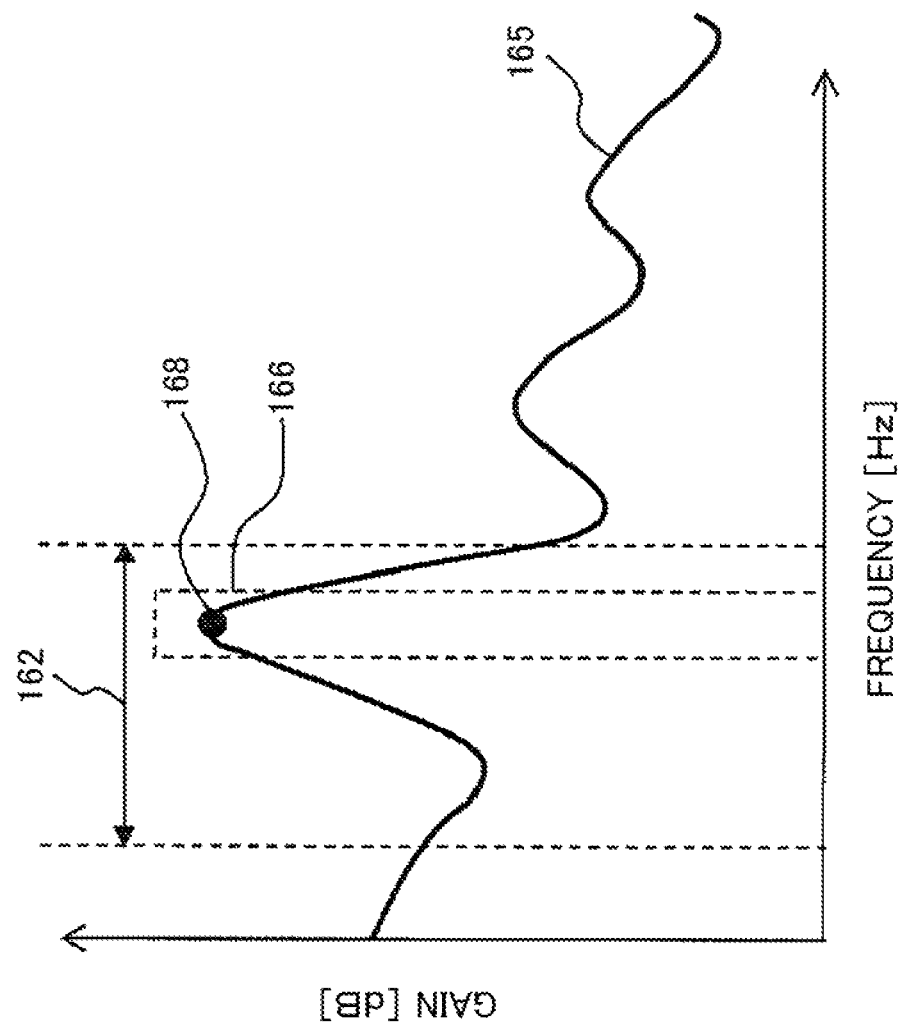

FIGS. 20 and 21 are diagrams illustrating setting examples of a bandwidth. In FIGS. 20 and 21, horizontal axes indicate a frequency [Hz], and vertical axes indicate a gain [dB]. In FIGS. 20 and 21, a heartbeat appearance band 162 is 0.8 to 4.0 Hz, for example.

According to a frequency analysis result (e.g. FFT result) 160 of a wireless sensor value illustrated in FIG. 20, a peak gain indicated by reference numeral 163 exists in the heartbeat appearance band 162. A frequency corresponding to the peak gain 163 is set to the center frequency of the BPF, and a bandwidth indicated by reference numeral 164 is set to the bandwidth of the BPF, for example.

Meanwhile, according to an FFT result 165 illustrated in FIG. 21, a peak gain indicated by reference numeral 168 exists in the heartbeat appearance band 162. The frequency corresponding to the peak gain 168 is set to the center frequency of the BPF.

Here, since the center frequency corresponding to the peak gain 168 is higher than the frequency corresponding to the peak gain 163 in FIG. 20, a bandwidth 166 narrower than the bandwidth 164 in FIG. 20 is set to the bandwidth of the BPF.

In this way, the center frequency of the BPF is set to the frequency corresponding to the reference heart rate, and the bandwidth is adaptively controlled according to a degree of the center frequency. Therefore, it is possible to efficiently remove a noise component which appears in the heartbeat appearance band.

In other words, by using the BPF which has the variable center frequency and variable bandwidth depending on heartbeat characteristics of a biological object, it is possible to efficiently remove an unnecessary signal component in the heartbeat appearance band without depending on a degree of the heart rate. Accordingly, it is possible to improve a detection accuracy of a heartbeat signal in the heartbeat appearance band.

FIG. 22 is a diagram illustrating an example of bandwidth information. Bandwidth information 170 illustrated in FIG. 22 may be stored in the memory 32 or the storage device 33 of the information processing apparatus 3, for example. As a non-restrictive example, the bandwidth information 170 may include reference heart rate information 171, BPF width lower limit information 172 and BPF width upper limit information 173.

The processor 31 of the information processing apparatus 3 is available to determine and set a band of the BPF corresponding to the reference heart rate with reference to the bandwidth information 170.

(Others)

In the above-described embodiments including the various examples, a wireless sensor such as a Doppler sensor is used as an example of a heartbeat sensor 21. However, the heartbeat sensor 21 may be a sensor such as an earclip which optically measures a change in a bloodstream, for example.

Even when a bloodstream amount changes due to a body motion, a body motion derived signal component is mixed as a noise component in a sensor detected signal, it is possible to efficiently remove the noise component by controlling the above-described variable BPF characteristics.

In case of the heartbeat sensor 21 which optically measures the change in the flood flow, even when a noise component is mixed in a sensor detected signal on the ground that external light is mixed in reflected light from the bloodstream in outdoor, the noise component can be removed by controlling the above-described variable BPF characteristics.

Further, the heartbeat sensor 21 may be an electrocardiograph or a phonocardiograph which measures a change in a potential of a heart muscle or a change in sound. Even when a body motion derived signal component is mixed as a noise component in a sensor detected signal on the ground that a user's muscle moves due to a body motion, it is possible to efficiently remove the noise component by controlling the above-described variable BPF characteristics.

Further, in the above-described embodiments including the various examples, the heartbeat sensor 21 and the inertial sensor 22 are integrated in the sensor unit 2. However, the heartbeat sensor 21 and the inertial sensor 22 may be provided in separate units as long as the heartbeat sensor 21 and the inertial sensor 22 are attached to the same user. In other words, it is not matter whether the heartbeat sensor 21 and the inertial sensor 22 are integrated or are provided in the separate units as long as a sensing target is the same user.

When the heartbeat sensor 21 and the inertial sensor 22 are integrated in the sensor unit 2, it is possible to omit a labor to individually manage the heartbeat sensor 21 and the inertial sensor 22 or attach the heartbeat sensor 21 and the inertial sensor 22 to the user. Therefore, it is possible to improve user-friendliness and convenience. Further, it is possible to prevent or suppress that one of the heartbeat sensor 21 and the inertial sensor 22 is left without being attached or is lost. Meanwhile, when the heartbeat sensor 21 and the inertial sensor 22 are provided in the separate units, it is possible to individually adjust attachment positions of the respective sensors 21 and 22 for the user. Therefore, it is expected that a degree of freedom in the attachment positions is improved.

All examples and conditional language provided herein are intended for pedagogical purposes to aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiment(s) of the present invention have been described in detail, it should be understood that the various changes, substitutions, and alterations could be made hereto without departing from the spirit and scope of the invention.

What is claimed is:

1. A sensor information processing apparatus comprising:
a receiver configured to receive a detected signal of a heartbeat sensor and a detected signal of an inertial sensor; and
a processor configured to control a target frequency band to be processed in the detected signal of the heartbeat sensor according to the detected signal of the inertial sensor, and calculate a heart rate based on a signal in the target frequency band of the detected signal of the heartbeat sensor, wherein the control includes:
  estimating the heart rate based on the detected signal of the inertial sensor;
  when the estimated heart rate is equal to or more than a threshold value, setting a center frequency of the target frequency band to a frequency corresponding to the estimated heart rate; and
  when the estimated heart rate is less than the threshold value, detecting the heart rate based on a result obtained by performing a frequency analysis on the detected signal of the heartbeat sensor, and setting the center frequency of the target frequency band to a frequency corresponding to the detected heart rate.

2. The sensor information processing apparatus according to claim 1, wherein the processor calculates a walking cadence based on the detected signal of the inertial sensor, and estimates the heart rate based on the walking cadence.

3. The sensor information processing apparatus according to claim 1, wherein the processor calculates a walking cadence based on the detected signal of the inertial sensor, calculates an exercise intensity based on the walking cadence, and estimates the heart rate based on the exercise intensity.

4. The sensor information processing apparatus according to claim 1, wherein the processor sets a bandwidth of the target frequency band to be narrowed as the estimated heart rate increases.

5. The sensor information processing apparatus according to claim 1, wherein the processor sets a bandwidth of the target frequency band to be narrowed as the detected heart rate increases.

6. The sensor information processing apparatus according to claim 1, wherein the heartbeat sensor is a radio wave sensor.

7. The sensor information processing apparatus according to claim 1, wherein the heartbeat sensor and the inertial sensor are provided in a sensor unit.

8. A sensor unit comprising:
  a heartbeat sensor;
  an inertial sensor; and
  a processor configured to control a target frequency band to be processed in the detected signal of the heartbeat sensor according to the detected signal of the inertial sensor, and calculate a heart rate based on a signal in the target frequency band of the detected signal of the heartbeat sensor, wherein the control includes:
  estimating the heart rate based on the detected signal of the inertial sensor;
  when the estimated heart rate is equal to or more than a threshold value, setting a center frequency of the target frequency band to a frequency corresponding to the estimated heart rate; and
  when the estimated heart rate is less than the threshold value, detecting the heart rate based on a result obtained by performing a frequency analysis on the detected signal of the heartbeat sensor, and setting the center frequency of the target frequency band to a frequency corresponding to the detected heart rate.

9. A computer-readable non-transitory recording medium having stored therein a sensor information processing program for causing a computer to execute a process comprising:
  controlling a target frequency band to be processed in a detected signal of a heartbeat sensor according to a detected signal of an inertial sensor; and
  calculating a heart rate based on a signal in the target frequency band of the detected signal of the heartbeat sensor, wherein the controlling includes:
  estimating the heart rate based on the detected signal of the inertial sensor;
  when the estimated heart rate is equal to or more than a threshold value, setting a center frequency of the target frequency band to a frequency corresponding to the estimated heart rate; and
  when the estimated heart rate is less than the threshold value, detecting the heart rate based on a result obtained by performing a frequency analysis on the detected signal of the heartbeat sensor, and setting the center frequency of the target frequency band to a frequency corresponding to the detected heart rate.

* * * * *